United States Patent
Blanchard et al.

(10) Patent No.: US 11,918,350 B2
(45) Date of Patent: Mar. 5, 2024

(54) SYSTEMS, METHODS, AND DEVICES FOR ROTATING INSULIN ADMINISTRATION SITES

(71) Applicant: The Translational Genomics Research Institute, Phoenix, AZ (US)

(72) Inventors: John Blanchard, Menlo Park, CA (US); Sampathkumar Rangasamy, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 419 days.

(21) Appl. No.: 17/217,711

(22) Filed: Mar. 30, 2021

(65) Prior Publication Data

US 2021/0298650 A1    Sep. 30, 2021

Related U.S. Application Data

(60) Provisional application No. 63/003,099, filed on Mar. 31, 2020.

(51) Int. Cl.
*A61B 5/145* (2006.01)
*A61B 5/00* (2006.01)
(Continued)

(52) U.S. Cl.
CPC .......... *A61B 5/14532* (2013.01); *A61B 5/746* (2013.01); *A61M 5/14244* (2013.01);
(Continued)

(58) Field of Classification Search
CPC .... A61B 5/14532; A61B 5/746; G16H 20/17; G16H 30/40; A61M 5/14244;
(Continued)

(56) References Cited

U.S. PATENT DOCUMENTS 7,722,535 B2   5/2010  Randlov et al.
8,924,161 B2  12/2014  Moerman
(Continued)

FOREIGN PATENT DOCUMENTS

CN        206295489 U   *  7/2017  ............ A61M 5/003

OTHER PUBLICATIONS

Muralidharan, S., et al. Mobile health technology in the prevention and management of type 2 diabetes. Indian J Endocrinol Metab 2017; 21(2):334-340.
(Continued)

*Primary Examiner* — Gabriel I Garcia
(74) *Attorney, Agent, or Firm* — KW Law, LLP

(57) ABSTRACT

An application running on a device to manage insulin site rotation may read a configuration file including a group, a plurality of sites in the group, and an image associated with the group. The application may detect an input selecting a site from the plurality of sites for administration of an insulin management device. The application may also set the selected site as unavailable for a predetermined duration in response to the input selecting the site. A log entry may be written to track usage of the site in response to the input selecting the site. A visual indicator on the selected site may show that the site is recently selected in response to detecting the input selecting the site within a predetermined duration. The insulin management device may be a pump, a syringe, or a glucose monitor.

20 Claims, 15 Drawing Sheets

(51) Int. Cl.
  *A61M 5/142*   (2006.01)
  *G16H 20/17*   (2018.01)
  *G16H 30/40*   (2018.01)
(52) U.S. Cl.
  CPC .............. *G16H 20/17* (2018.01); *G16H 30/40* (2018.01); *A61M 2005/14208* (2013.01); *A61M 2202/0007* (2013.01); *A61M 2205/3327* (2013.01); *A61M 2230/201* (2013.01)
(58) Field of Classification Search
  CPC ........... A61M 2205/14208; A61M 2005/3327; A61M 2202/0007; A61M 2230/201
  USPC ......................................................... 382/128
  See application file for complete search history.

(56) References Cited

U.S. PATENT DOCUMENTS

| | | | |
|---|---|---|---|
| 10,046,119 B2 | 8/2018 | Boyden et al. | |
| 10,173,015 B2 | 1/2019 | Fiedler et al. | |
| 10,293,101 B2 | 5/2019 | Brewer et al. | |
| 11,517,659 B2* | 12/2022 | Farzam | A61M 5/427 |
| 11,534,553 B2* | 12/2022 | Patil | A61M 5/3158 |
| 11,627,944 B2* | 4/2023 | Savitsky | G09B 23/286 |
| | | | 600/437 |
| 2007/0012322 A1 | 1/2007 | Ragg | |
| 2009/0177154 A1 | 7/2009 | Blomquist | |
| 2013/0172688 A1 | 7/2013 | Allen et al. | |
| 2014/0324445 A1 | 10/2014 | Carlsgaard et al. | |
| 2017/0028141 A1* | 2/2017 | Fiedler | A61M 5/003 |

OTHER PUBLICATIONS

Kashgary, A., et al. The role of mobile devices in doctor patient communication: a systematic review and meta-analysis. J Telemed Telecare 2017; 23(8):693-700.
Chavez, S., et al. Mobile apps for the management of diabetes. Diabetes Care 2017; 40(10):e145 e146.
Radermecker, R. P., et al. Lipodystrophy reactions to insulin: effects of continuous insulin infusion and new insulin analogs. Am J Clin Dermatol 2007; 8(1):21-28.
Breznik, V., et al. Insulin-induced localized lipoatrophy. Acta Dermatovenerol Alp Panonica Adriat 2013; 22(4):83-8.
Hauzenberger, J. R., et al. Detailed analysis of insulin absorption variability and the tissue response to continuous subcutaneous insulin infusion catheter implantation in swine. Diabetes Technol Ther 2017; 19(11):641-650.
Hauzenberger, J. R., et al. Systematic in vivo evaluation of the timedependent inflammatory response to steel and Teflon insulin infusion catheters. Sci Rep 2018; 8(1):1132.
Sahasrabudhe, R. A., et al. Insulin injection site adverse effect in a type 1 diabetes patient: an unusual presentation. J Clin Diagn Res 2017; 11(8):OD10-OD11.
Kaltheuner, L., et al. Lipohypertrophic skin changes in patients with diabetes: visualization by infrared images. J Diabetes Sci Technol 2018; 12(6):1152-1158.
Schoenbrum, M. (2014). ShotPut [Mobile app]. App Store. Retrieved from http://www.MyShotPut.com.
Criosoft LLC. (2019). Injection Tracker & Reminder [Mobile App]. App Store. Retrieved from http://criosoft.com/schedule/.
Mylan Inc. (2014). Mylan Smart Injection Tracker [Mobile App]. App Store. Retrieved from https://appadvice.com/app/mylan-smart-injection-tracker/881604585.
Andrews, J. (2018). Left Side Right [Mobile App]. App Store. Retrieved from https://apps.apple.com/us/app/left-side-right/id1420599045.
Shotput. Home page, Jul. 6, 2019; accessed online on Apr. 27, 2021 at: https://web.archive.org/web/20190706155843/http://myshotput.com/.
Shotput. User Guide V2.1, May 28, 2019; accessed online on Apr. 27, 2021 at: https://web.archive.org/web/20190528084158/http://myshotput.com/documnetation-in-englishv2-1/.
Jahns, R-G. Today's diabetes apps are far away from meeting the seven best practice standards, Oct. 21, 2020; accessed online Apr. 27, 2021 at: https://web.archive.org/web/20201021051600/https://research2guidance.com/todays-diabetes-apps-are-far-away-from-meeting-the-seven-best-practice-standards-2/.
Moore, P.A., et al. Diabetes: a growing epidemic of all ages. J Am Dent Assoc 2003; 134 Spec No. 11S-15S.
American Diabetes Association. 2. Classification and Diagnosis of Diabetes: Standards of Medical Care in Diabetes-2018. Diabetes Care 2018; 41(Suppl 1):S13-S27.
Grunberger, G., et al. Consensus Statement by the American Association of Clinical Endocrinologists/American College of Endocrinology insulin pump management task force. Endocr Pract 2014; 20(5):463-489.
Senn, J-D., et al. Long-Term Effects of Initiating Continuous Subcutaneous Insulin Infusion (CSII) and Continuous Glucose Monitoring (CGM) in People with Type 1 Diabetes and Unsatisfactory Diabetes Control. J Clin Med 2019; 8(3):394.
Forbes, J. M., et al. Mechanisms of diabetic complications. Physiol. Rev. 2013; 93(1):137-188.
Laing, S. P., et al. Mortality from heart disease in a cohort of 23,000 patients with insulin-treated diabetes. Diabetologia 2003; 46(6):760-765.
Marcovecchio, M .L., et al. A new strategy for vascular complications in young people with type 1 diabetes mellitus. Nat Rev Endocrinol 2019; 15(7):429-435.
Groat D., et al. Self-Management Behaviors in Adults on Insulin Pump Therapy. J Diabetes Sci Technol 2017; 11(2):233-239.
O'connell, M. A., et al. Poor adherence to integral daily tasks limits the efficacy of CSII in youth. Pediatr Diabetes 2011; 12(6):556-559.
Hendricks, M., et al. A profile of self-care behaviors in emerging adults with type 1 diabetes. Diabetes Educ 2013; 39(2):195-203.
Groat, D., et al. Design and Testing of a Smartphone Application for Real-Time Self-Tracking Diabetes Self-Management Behaviors. Appl Clin Inform 2018; 9(2):440-449.
Grando, M. A., et al. Characterization of Exercise and Alcohol Self-Management Behaviors of Type 1 Diabetes Patients on Insulin Pump Therapy. J Diabetes Sci Technol 2017; 11(2):240-246.
Deshkar, S., et al. A Review of IoT based m-Health Systems for Diabetes. International Journal of Computer Science and Telecommunications 2017; 8(1):13-18.
Giannini, C., et al. Technology and the issue of cost/benefit in diabetes. Diabetes Metab Res Rev 2009; 25 Suppl 1:S34-44.
Pickup, J. C., et al. Continuous subcutaneous insulin infusion in the treatment of diabetes mellitus. Diabetes Care 1980; 3(2):290-300.
Deeb, A., et al. Impact of Insulin Injection and Infusion Routines on Lipohypertrophy and Glycemic Control in Children and Adults with Diabetes. Diabetes Ther 2019; 10(1):259-267.
Frid, A. H., et al. Worldwide injection technique questionnaire study: population parameters and injection practices. Mayo Clin Proc 2016; 91(9):1212-1223.
Messer, L. H., et al. Preserving Skin Integrity with Chronic Device Use in Diabetes. Diabetes Technol Ther 2018; 20(S2):S254-S264.
Richardson, T., et al. Skin-related complications of insulin therapy: epidemiology and emerging management strategies. Am J Clin Dermatol 2003; 4(10):661-667.
Sullivan, C.A. , et al. An atypical presentation of insulin amyloidosis: an uncommon but important complication of Insulin therapy. AACE Clinical Case Reports 2017; 4(1):80-83.
Conwell L. S., et al. Dermatological complications of continuous subcutaneous insulin infusion in children and adolescents. J Pediatr 2008; 152(5):622-628.
Pleus, S., et al. Documentation of Skin-Related Issues Associated with Continuous Glucose Monitoring Use in the Scientific Literature. Diabetes Technol Ther 2019; 21(10):538-545.
Famulla, S., et al. Insulin injection into lipohypertrophic tissue: blunted and more variable insulin absorption and action and impaired postprandial glucose control. Diabetes Care 2016; 39(9):1486-1492.

(56) References Cited

OTHER PUBLICATIONS

Volkova, N. I., et al. Clinical significance of lipohypertrophy without visual and palpable changes detected by ultrasonography of subcutaneous fat. Ter Arkh 2019; 91(4):62-66; Abstract Only.

Improta, M. R., et al. Lessons learned from an unusual case of severe hypoglycemia. Diabetes Metab Syndr 2019; 13(2):1237-1239.

Barola, A., et al. Insulinmediated lipohypertrophy: an uncommon cause of diabetic ketoacidosis. BMJ Case Rep 2017; 2017:bcf2017220387.

Al-Hayek, A. A., et al. Frequency and associated risk factors of recurrent diabetic ketoacidosis among Saudi adolescents with type 1 diabetes mellitus. Saudi Med J 2015; 36(2):216-220.

Al Ajlouni, M., et al. Prevalence of lipohypertrophy and associated risk factors in insulin-treated patients with type 2 diabetes mellitus. Int J Endocrinol Metab 2015; 13(2):e20776.

Sahasrabudhe, R .A., et al. Unexplained Persistent Hyperglycemia in a Type I Diabetes Patient—Is Injection Site Lipohypertrophy the Cause? J Clin Diagn Res 2016; 10(9):OD05-OD06.

Gentile, S., et al. Insulin-Related Lipohypertrophy in Hemodialyzed Diabetic People: a Multicenter Observational Study and a Methodological Approach. Diabetes Ther 2019; 10(4):1423-1433.

Gradel, A. K. J., et al. Factors affecting the absorption of subcutaneously administered insulin: effect on variability. J Diabetes Res 2018; 2018:1205121.

Evert, A. B., et al. Improving patient experience with insulin infusion sets: practical guidelines and future directions. Diabetes Educ 2016; 42(4):470-484.

Al Hayek, A. A., et al. Frequency of Lipohypertrophy and Associated Risk Factors in Young Patients with Type 1 Diabetes: a Cross-Sectional Study. Diabetes Ther 2016; 7(2):259-267.

Hildebrandt, P., et al. Diffusion and polymerization determines the insulin absorption from subcutaneous tissue in diabetic patients. Scand J Clin Lab Invest 1985; 45(8):685-690.

Galloway, J. A., et al. Factors influencing the absorption, serum insulin concentration, and blood glucose responses after injections of regular insulin and various insulin mixtures. Diabetes Care 1981; 4(3):366-376.

Kølendorf, K., et al. Clinical factors influencing the absorption of 125I-NPH insulin in diabetic patients. Horm Metab Res 1983; 15(6):274-278.

Koivisto, V. A., et al. Alterations in insulin absorption and in blood glucose control associated with varying insulin Injection sites in diabetic patients. Ann Intern Med 1980; 92(1):59-61.

Bantle, J. P., et al. Rotation of the Anatomic Regions Used for Insulin Injections and Day-to-Day Variability of Plasma Glucose in Type I Diabetic Subjects. JAMA 1990; 263(13):1802-1806.

Yuan, J., et al. Can the upper inner side of the thigh become a new option for insulin injection? Curr Med Res Opin 2016; 32(7):1319-1324.

Spollett, G., et al. Improvement of insulin injection technique: examination of current issues and recommendations. Diabetes Educ 2016; 42(4):379-394.

Saltiel-Berzin, R., et al. Translating the research in insulin injection technique: implications for practice. Diabetes Educ 2012; 38(5):635-643.

Frid, A., et al. New injection recommendations for patients with diabetes. Diabetes Metab 2010; 36 Suppl 2:S3-18.

Zimmet P., et al. Global and societal implications of the diabetes epidemic. Nature 2001; 414(6865):782-787.

Garabedian, L. F., et al. Mobile Phone and Smartphone Technologies for Diabetes Care and Self-Management. Curr Diab Rep 2015; 15(12):109.

Quinn, C. C., et al. Older Adult Self-Efficacy Study of Mobile Phone Diabetes Management. Diabetes Technol Ther 2015; 17(7):455-461.

Fatehi, F., et al. Mobile health (mhealth) for diabetes care: opportunities and challenges. Diabetes Technol Ther 2017; 19(1):1-3.

Quinn, C. C., et al. Mobile diabetes intervention study of patient engagement and impact on blood glucose: mixed methods analysis. JMIR Mhealth Uhealth 2018; 6(2):e31.

\* cited by examiner

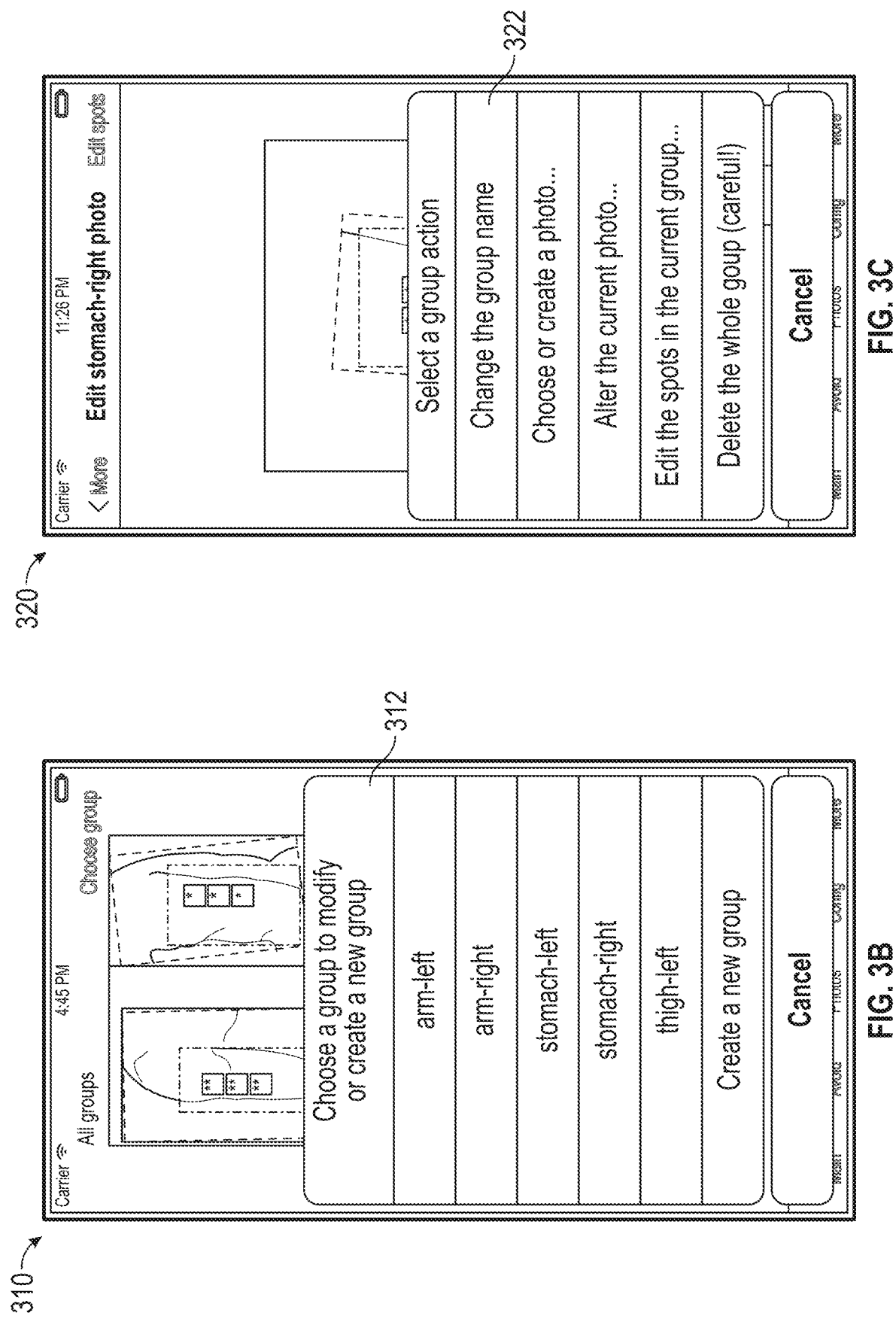

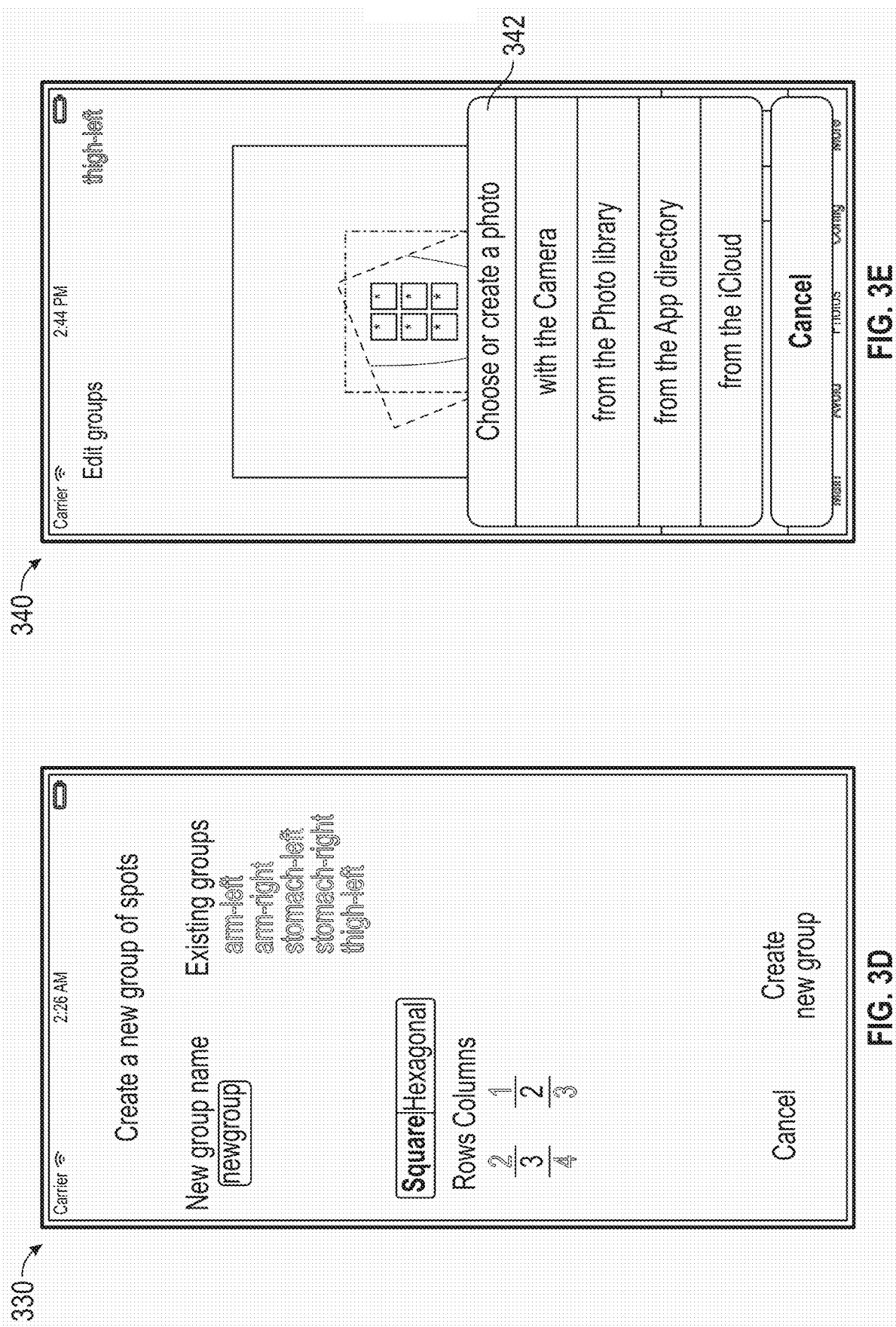

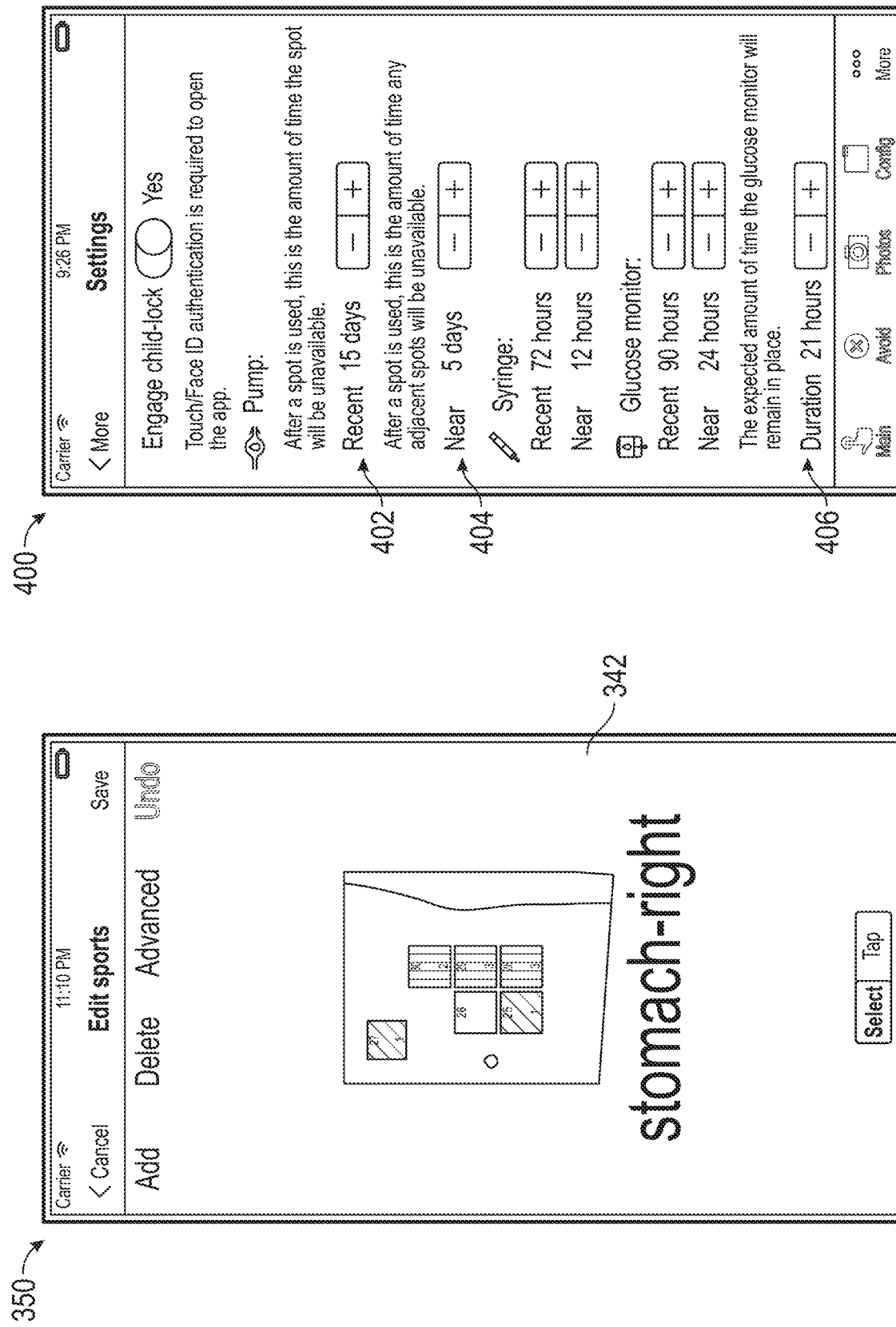

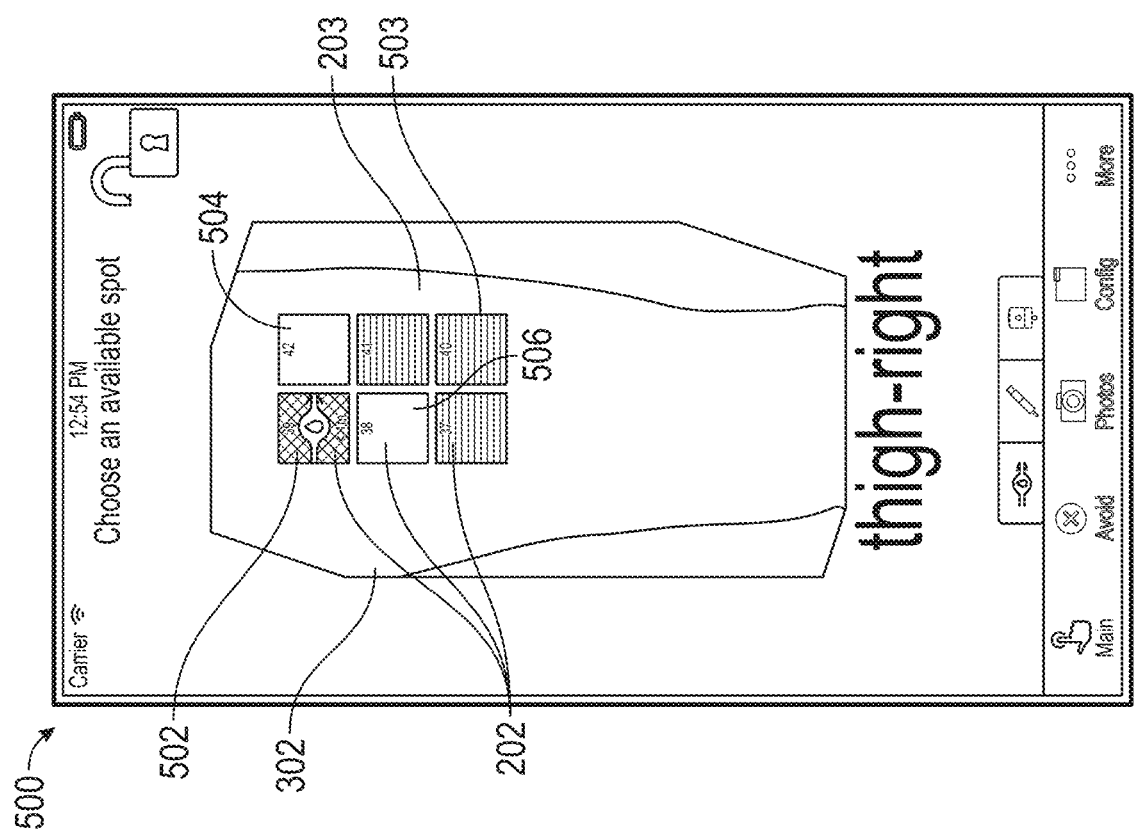
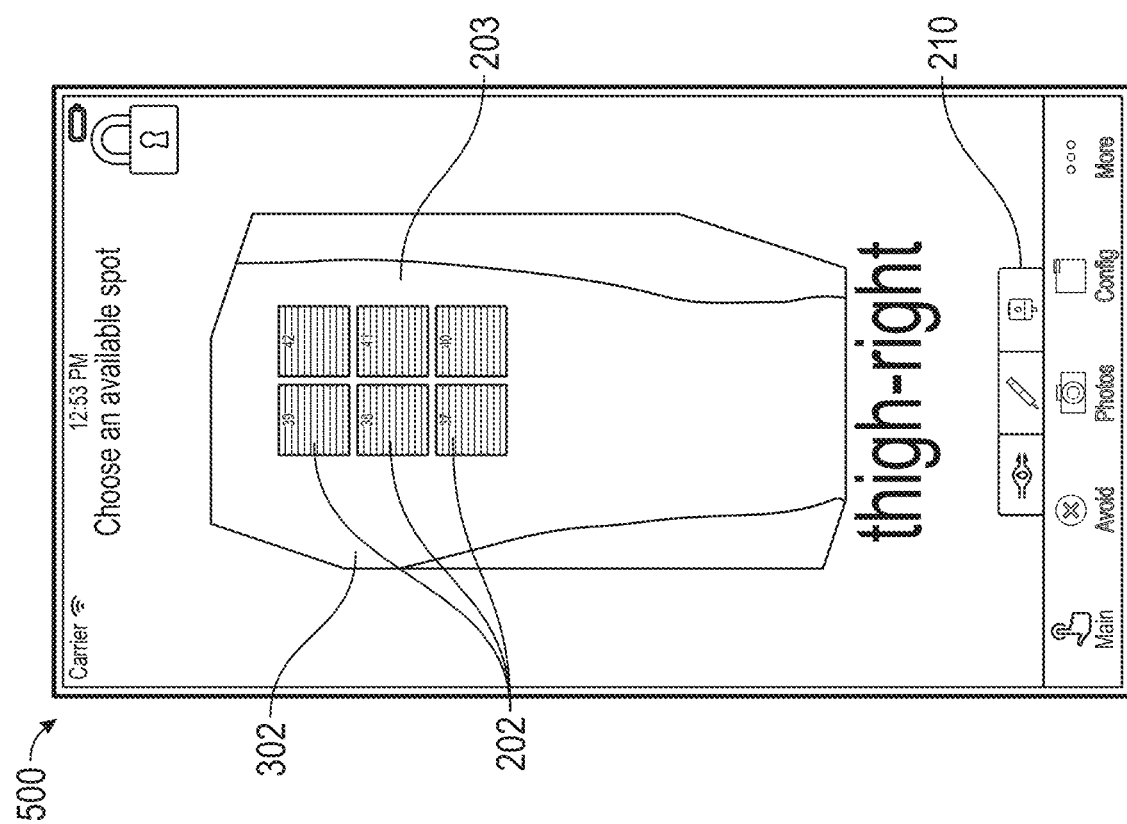
FIG. 5B
FIG. 5A

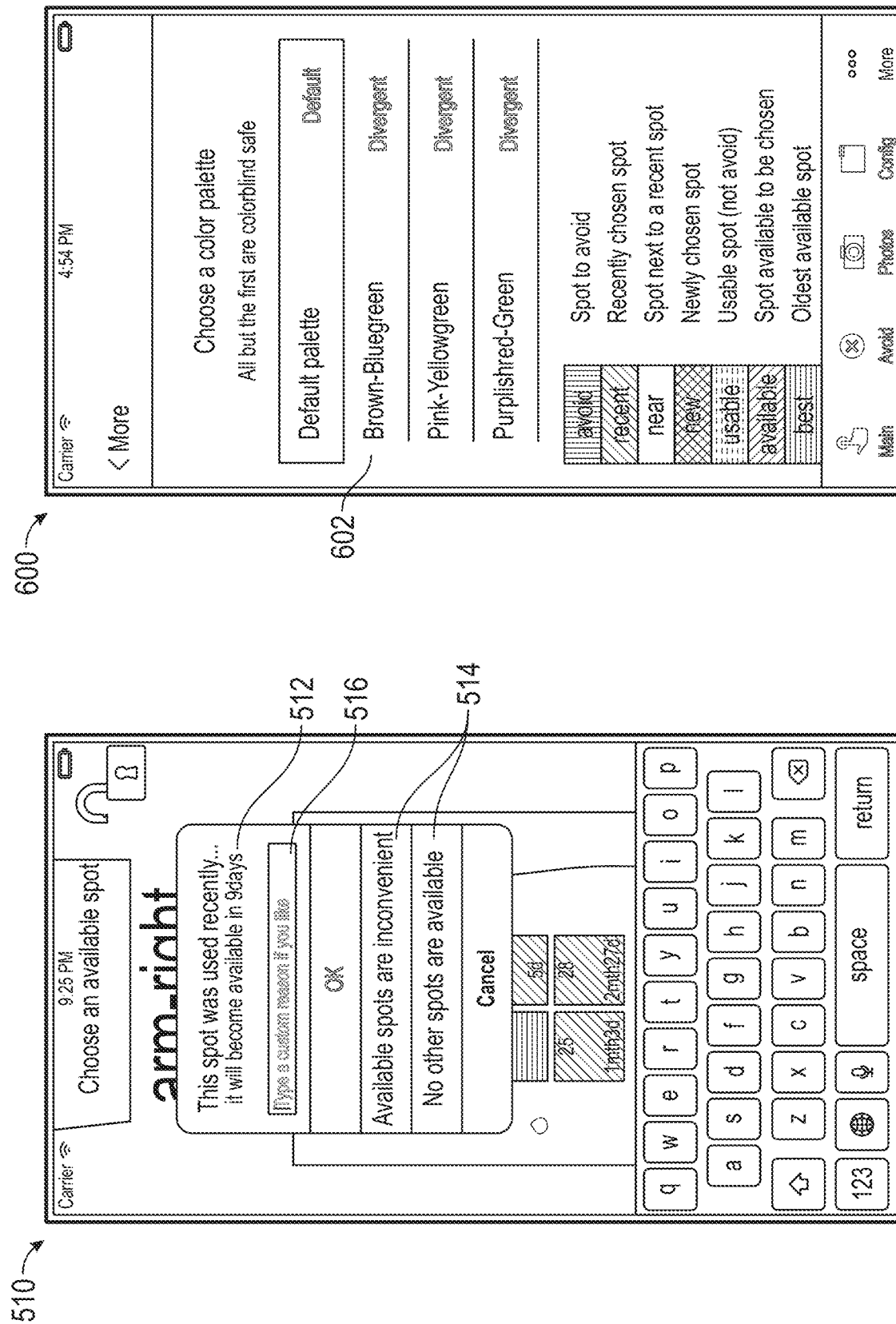

- 708 — Remove rows...
- 702 — 2020 March
  - newgroup: 35 — 2020-03-09 21:31:06
  - Available spots are inconvenient
- 704 — stomach-right: 28 — 2020-03-09 21:28:27
- 703 — 2020 January
- 706 — newgroup: 32 — 2020-01-25 01:54:47
  - arm-left: 11 — 2020-01-22 15:38:04
  - stomach-right: 29 — 2020-01-14 14:49:14
  - Available spots are inconvenient
- 709 — stomach-right: 29 — 2020-01-14 14:47:41
  - No other spots are available
  - arm-right: 7 — 2020-01-13 10:30:46

Main | Avoid | Stats | History | More

< Spot history    Edit history item    Save

- Group: newgroup
- Index: 35
  - newgroup 33
  - newgroup 34
  - newgroup 35
  - newgroup 36
  - newgroup 37
- Type:
- Date: 2020-03-09
  - February   8   2019
  - March   9   2020
  - April   10   2021
- Time: 21:31:06
  - 8   30   AM
  - 9   31   PM
  - 10   32

Override: "Available spots are inconvenient"
Change override

SYSTEMS, METHODS, AND DEVICES FOR ROTATING INSULIN ADMINISTRATION SITES

CROSS-REFERENCE TO RELATED APPLICATIONS

This application claims priority to U.S. Provisional Application No. 63/003,099, filed on Mar. 31, 2020, which is incorporated herein in its entirety for any purpose.

FIELD

The present disclosure relates to rotating sites for insulin management. In particular, systems, methods, and devices of the present disclosure enable accurate site rotation of insulin management devices.

BACKGROUND

Diabetes mellitus is the most common endocrine disease in children (type 1 diabetes) and adults (type 2 diabetes), affecting more than 30 million Americans. All type 1 diabetics use exogenous insulin for life due to the loss of insulin-producing beta cells. Effective treatment includes multiple insulin injections per day or continuous subcutaneous insulin infusion (CSII) to maintain a blood glucose level in the normal range throughout the day. The goal of glycemic management in any diabetic patient is to maintain blood glucose levels in a desired target range and avoid blood glucose swings between low (hypoglycemia) and high glucose (hyperglycemia) levels. Poor glycemic control in diabetes leads to devastating micro- and macro-vascular complications including kidney damage (diabetic nephropathy), eye damage (diabetic retinopathy), brain (diabetic stroke), and cardiovascular disease (CVD).

Self-management behaviors (SMBs) in patients with diabetes have shown to improve the adherence to standard treatment protocols. Tools that enable SMBs in diabetic subjects lead to better glycemic control and reduce risk of diabetes related complications. Patient empowering SMBs include blood glucose monitoring, self-administration of insulin bolus injections, monitoring food, glycemic index calculations, and exercise. Various tools, such as bolus calculators, hyper- and hypoglycemia warnings embedded in glucose meters and insulin pumps, are intended to assist patients to accurately dose their insulin requirements. Despite the revolutionary nature of these tools, they tend to be most effective with constant involvement by the user and caregivers.

Prolonged injection of insulin at a single location can result in tissue damage and decrease the diffusion characteristics of the location. For example, treatment standards recommend moving an insulin pump to a new location after an insulin pump has stayed in position for several days. This allows the site to recover from the insulin infusion. Timely site rotation with insulin injection or CSII has been shown to significantly reduce the risk of skin pathologies such as infection, flare, skin injury, scarring, irritation, allergic reactions, abscess, amyloidosis and hyperkeratosis, pump and bumps. Long term insulin injection or infusion through pump therapy in type 1 diabetes is significantly associated with lipodystrophy, a condition with abnormal distribution of fat in the body characterized by lipoatrophy (loss of fat) or lipohypertrophy (accumulation of fat tissue). Diagnosis of lipodystrophy is strongly correlated with non-rotation of sites used for insulin management devices. Most people with type 1 diabetes experience lipohypertrophy at some point due to improper site rotation.

SUMMARY

Systems, methods, and devices (collectively, the "System") of the present disclosure may include an application running on a device and reading a configuration file including a group, a plurality of sites in the group, and an image associated with the group. The application may detect an input selecting a site from the plurality of sites for administration of an insulin management device. The application may also set the selected site as unavailable for a predetermined duration in response to the input selecting the site. A log entry may be written to track usage of the site in response to the input selecting the site.

In various embodiments, the application may create a new image associated with the group and overlay the sites in the group on the new image. A first visual indicator on the selected site may show that the site was recently selected in response to detecting the input selecting the site within a predetermined duration. A second visual indicator on the selected site may show that the site is unavailable in response to a first period greater than the predetermined duration lapsing since detecting the input selecting the site. A recent parameter associated with the insulin management device may be set in response to reading the configuration file. A third visual indicator on the selected site may show that the site is available in response to a period greater than the recent parameter lapsing since detecting the input selecting the site. The insulin management device may be a pump, a syringe, or a glucose monitor.

In various embodiments, the application may send a notification to a second device in response to the insulin management device being in place longer than the predetermined duration. The application may override the unavailable flag in response to receiving a justification from an override interface. A statistics interface may include site counts, override justifications, and insulin usage by site. The application may estimate insulin diffusion sensitivity in response to insulin usage at the selected site, data from the insulin management device, exercise data, and carbohydrate data. The site may be suggested for use in response to historic site usage and insulin diffusion sensitivity. The insulin management device may generate closed-loop data to support suggesting the site for use. The insulin management device may be a portable infusion pump, a cannula inserter, a needleless jet injector, a system with a separate drug reservoir, or an implantable drug pump.

The System may include a process for rotating insulin administration sites with an application running on a device. The application may read a configuration file including a plurality of insulin administration sites having locations on a 3-dimensional model of a body. The application may render sites over an image of a body part associated with the 3-dimensional model of the body. A selected site from the plurality of sites may be identified for placement of an insulin management device. The application may set an unavailable flag for the selected site for a predetermined duration in response to detecting the selected site. The application running on the device may rotate the image of the body part associated with the 3-dimensional model in response to a user input.

In various embodiments, the application may identify the selected site in response to historic site usage and insulin diffusion sensitivity at the selected site. A camera of the device may capture a video of a part of the body associated with the 3-dimensional model, and the device may render the sites over the video in real-time.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the illustrations.

FIG. 3B illustrates an exemplary interface for selecting or creating images, groups, and sites for modification, in accordance with various embodiments;

FIG. 3C illustrates an exemplary interface for modifying or creating images, names, and sites associated with a group of insulin administration sites, in accordance with various embodiments;

FIG. 3D illustrates an exemplary interface for creating a group of insulin administration sites, in accordance with various embodiments;

FIG. 3E illustrates an exemplary interface for creating or uploading an image of a location on a body suitable for insulin administration sites, in accordance with various embodiments;

FIG. 3F illustrates an exemplary interface for manipulating sites and groups overlaid on an image, in accordance with various embodiments;

FIG. 4 illustrates an exemplary interface for configuring an insulin rotation application with rest durations, in accordance with various embodiments;

FIG. 5A illustrates a group of insulin administration sites available for use and overlaid on an image of a body part, in accordance with various embodiments;

FIG. 5B illustrates a group of insulin administration sites overlaid on an image of a body part with one of the sites newly selected for use by an insulin pump, in accordance with various embodiments;

FIG. 5E illustrates an override interface to reuse an insulin administration site before a resting period has lapsed, in accordance with various embodiments;

FIG. 6 illustrates an exemplary interface for selecting visual indicators indicative of status at insulin administration sites, in accordance with various embodiments;

FIG. 7A illustrates an exemplary interface for reviewing or editing historic usage of insulin management devices, in accordance with various embodiments;

FIG. 7B illustrates an exemplary interface for editing a log entry memorializing usage of an insulin management device, in accordance with various embodiments;

DETAILED DESCRIPTION

The detailed description of exemplary embodiments herein refers to the accompanying drawings, which show exemplary embodiments by way of illustration and their best mode. While these exemplary embodiments are described in sufficient detail to enable those skilled in the art to practice the inventions, it should be understood that other embodiments may be realized, and that logical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Systems, methods, and devices of the present disclosure intuitively guide users in the placement of insulin pumps, insulin pens, and glucose monitors and track the position history to enable site rotation. Users may select spots for pump placement to track the location of use, duration of use, date of use, or type of use at a location to reduce the likelihood of poor site rotation. In that regard, systems, methods, and devices of the present disclosure may assist various users (e.g., patients, parents, caregivers, medical professionals, etc.) that rotate injection sites for diabetics (type 1 or type 2) in tracking their injection site history to encourage safe and accurate site rotation.

Figure 1A:
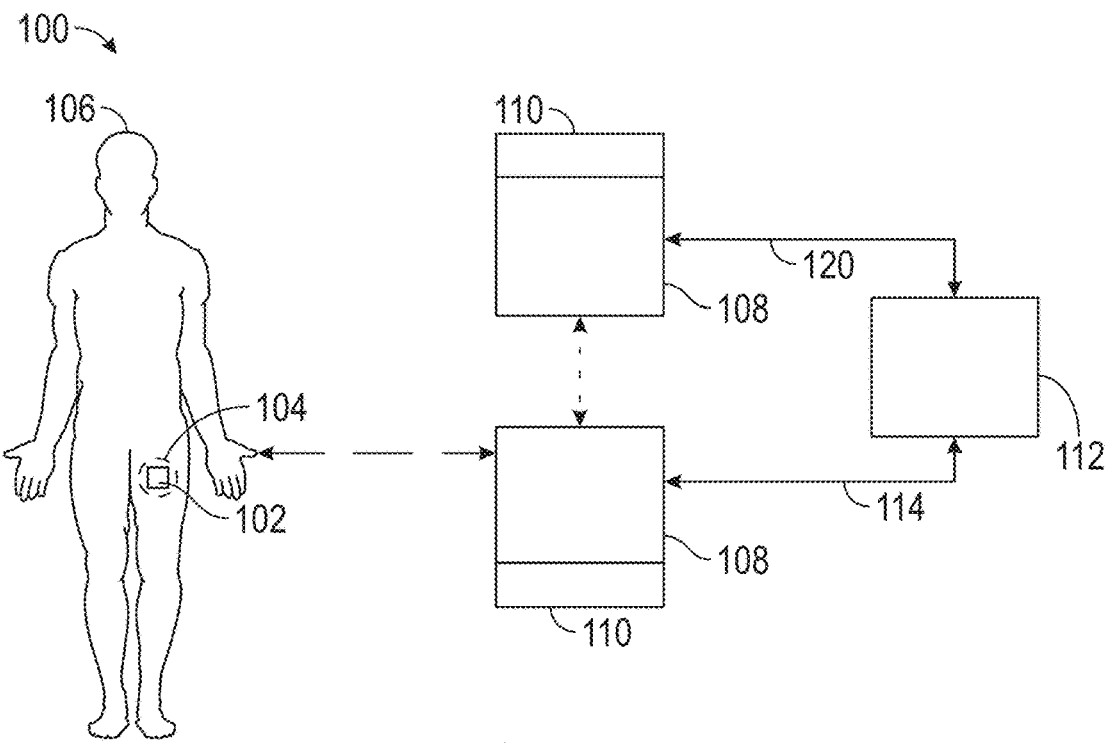
FIG. 1A illustrates an exemplary system for rotating insulin administration and glucose monitoring sites, in accordance with various embodiments.

With reference to FIG. 1A, computer-based system 100 is shown for use in rotating insulin injection and/or blood draw sites, in accordance with various embodiments. Insulin rotation system 100 may comprise insulin management device 102 deployed at a site 104 on body 106 of a patient or application user. Insulin management device 102 may be an insulin pump, a syringe, a glucose monitor, a blood draw device, an insulin administration device, a portable infusion pump, a cannula inserter, a needleless jet injector, a system with a separate drug reservoir, an implantable drug pump, or any other blood related device configured to penetrate the skin of body 106 or administer a drug. The user or patient may use device 108 running insulin rotation application 110 to upload, record, capture, or otherwise input information relating to use of insulin management device 102 at site 104. Device 108 may comprise a computing device such as, for example, a smartphone, tablet, personal computer, laptop, remote host, virtual desktop, or other computing device capable of detecting inputs and displaying outputs. Computing device 108 may comprise one or more processors in communication with a tangible, non-transitory memory configured to execute operations in response to execution by a processor of instructions stored in memory. Computing device 108 may be in electronic communication with insulin management device 102 to log activity of insulin management device 102 and integrate data from insulin management device 102 into insulin rotation application 110.

Figure 1B:
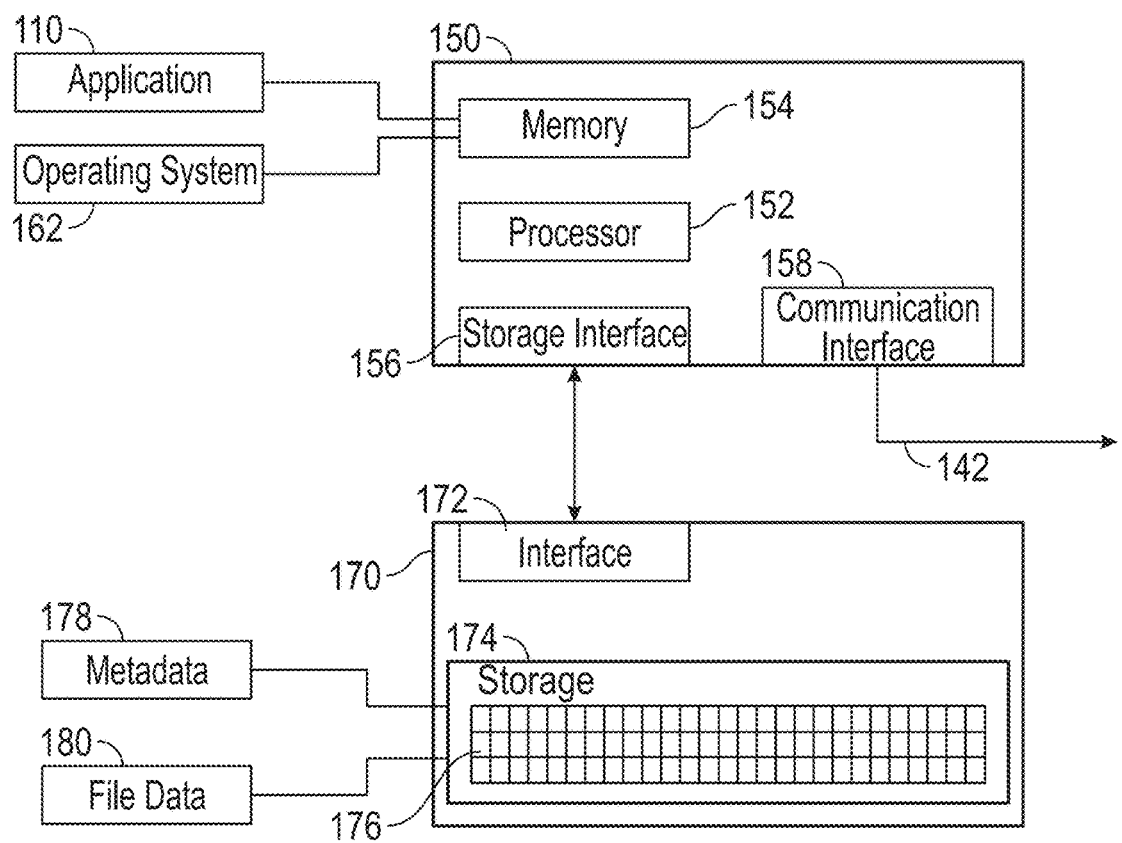
FIG. 1B illustrates an exemplary computing device for use in a system for rotating insulin administration and glucose monitoring sites, in accordance with various embodiments.

With reference to FIG. 1B and continued reference to FIG. 1A, one or more devices 108 may include various electronic components such as, for example, a processing component 150 and a storage component 170. One or more devices 108 may include one or more user interfaces, for input or output such as a keyboard, mouse, track ball, touch pad, touch screen, and/or a display. Each processing component 150 may include a processor 152 and a memory 154. Memory 154 may be in electronic communication with processor 152. Processor 152 may include one or more microprocessors, co-processors, logic devices, and/or the like. Processor 152 comprising multiple microprocessors may execute in parallel or asynchronously. The logic device may include, for example, analog-to-digital converters, digital-to-analog converters, buffers, multiplexers, clock circuits, or any other peripheral devices supporting operation of processor 152. Memory 154 may include a single memory device or multiple memory devices and may be volatile memory, non-volatile memory, or a combination thereof.

Each processing component 150 may also comprise a storage interface 156 in electronic communication with processor 152. Storage interface 156 may be configured to provide a physical connection to storage component 170. For example, in response to storage component 170 comprising an internal hard drive, storage interface 156 may include, for example, appropriate cables, drivers, and the like to enable the physical connection. As a further example, in response to storage component 170 comprising a removable storage medium, such as a CD-ROM drive, DVD-ROM drive, USB drive, memory card, and the like, storage interface 156 may comprise an interface, a port, a drive, or the like configured to receive the removable storage medium and any additional hardware suitable to operate the interface, the port, the drive, or the like.

Each processing component 150 may also comprise a communication interface 158 in electronic communication with processor 152. Communication interface 158 may be, for example, a serial communication port, a parallel communication port, an Ethernet communication port, or the like. Device 108 may comprise a communication medium 142. Communication medium 142 may be configured to enable electronic communication between processing component 150 and network 114 (of FIG. 1A). Communication medium 142 may be a cable, such as an Ethernet cable. In various embodiments, communication interface 158 may be configured for wireless communication via infrared, radio frequency (RF), optical, BLUETOOTH®, or other suitable wireless communication methods. Communication medium 142 may comprise one or more antennas configured to enable communication over free space. Network 114 and/or network 120 may comprise an intranet, the Internet, or a combination thereof. Each device 108 in system 100 may communicate with another device either directly or indirectly via network 114 or network 120.

In various embodiments, storage component 170 may comprise any suitable database, data structure, unstructured data store, relational database, document-based database or the like capable of storing and/or maintaining data. Storage component 170 may comprise, for example, a hard drive, a solid-state drive, magnetic tape, a removable memory card, an array of drives, and the like. Storage component 170 may comprise an interface 172 configured to enable communications with processing component 150, via storage interface 156. For example, storage interface 156 in processing component 150 and interface 172 in the storage component 170 define the physical layers between the processing component 150 and storage component 170, respectively, establishing communication therebetween. In various embodiments, storage component 170 includes storage 174, with multiple blocks 176, in which data and files are saved. Each file stored in the storage component 170 may include metadata 178 and file data 180. Metadata 178 for a file includes, for example, pointers to particular blocks 176 in storage 174 at which the file data 180 for the file is stored. File data may include data stored in nonvolatile storage to render a visual representation of a document or artifact to a user, launch an application, load an application into a predetermined state, retain historic application data, read or write blocks from memory 154, boot an operating system, or otherwise serve as a more permanent storage location than memory 154 for processing component 150.

In various embodiments, processor 152 in each device 108 may be configured to execute insulin rotation application 110 and an operating system 162 suitable to run on device 108. Operating system 162 allocates resources of device 108 and hosts services common between insulin rotation application 110 executing on processor 152 and memory 154. Operating system 162 may be stored on storage component 170, within memory 154, or a combination thereof depending on configuration and state of device 108. Operating system 162 may vary between devices 108 and is configured to control the hardware components for the associated type of device 108. For example, a device 108 in the form of a computer might run Windows® or Linux® as operating system 162, but a device 108 in the form of a smartphone may run Android® or iOS® as operating system 162. Other devices may run custom operating systems embedded on programmable memory. Processor 152 may be configured to execute operating system 162 and each of the applications 110 stored in memory 154 or storage component 170.

In various embodiments, insulin rotation application 110 may comprise an executable, device driver, application programming interface (API), or other such routine or protocol. Application 110 may be deployed at the data access layer, stored in memory 154, or on storage component 170 and configured to be loaded onto the device 108 and managed or operated by operating system 162. During power-up of the device 108, during initialization of operating system 162, or in response to a user selecting application 110, operating system 162 detects the presence of and launches application 110. In response to launching, application 110 may monitor input devices and respond to inputs using system calls to read or write storage 174 or memory 154, execute routines on processor 152, communicate through communication interface 158, or otherwise respond to detected inputs. Application 110 may include a program written in a programming language such as, for example, Go, Java®, Koltin®, Swift, Solidity, Python®, or any other suitable programming language.

Figures 2, 3A:
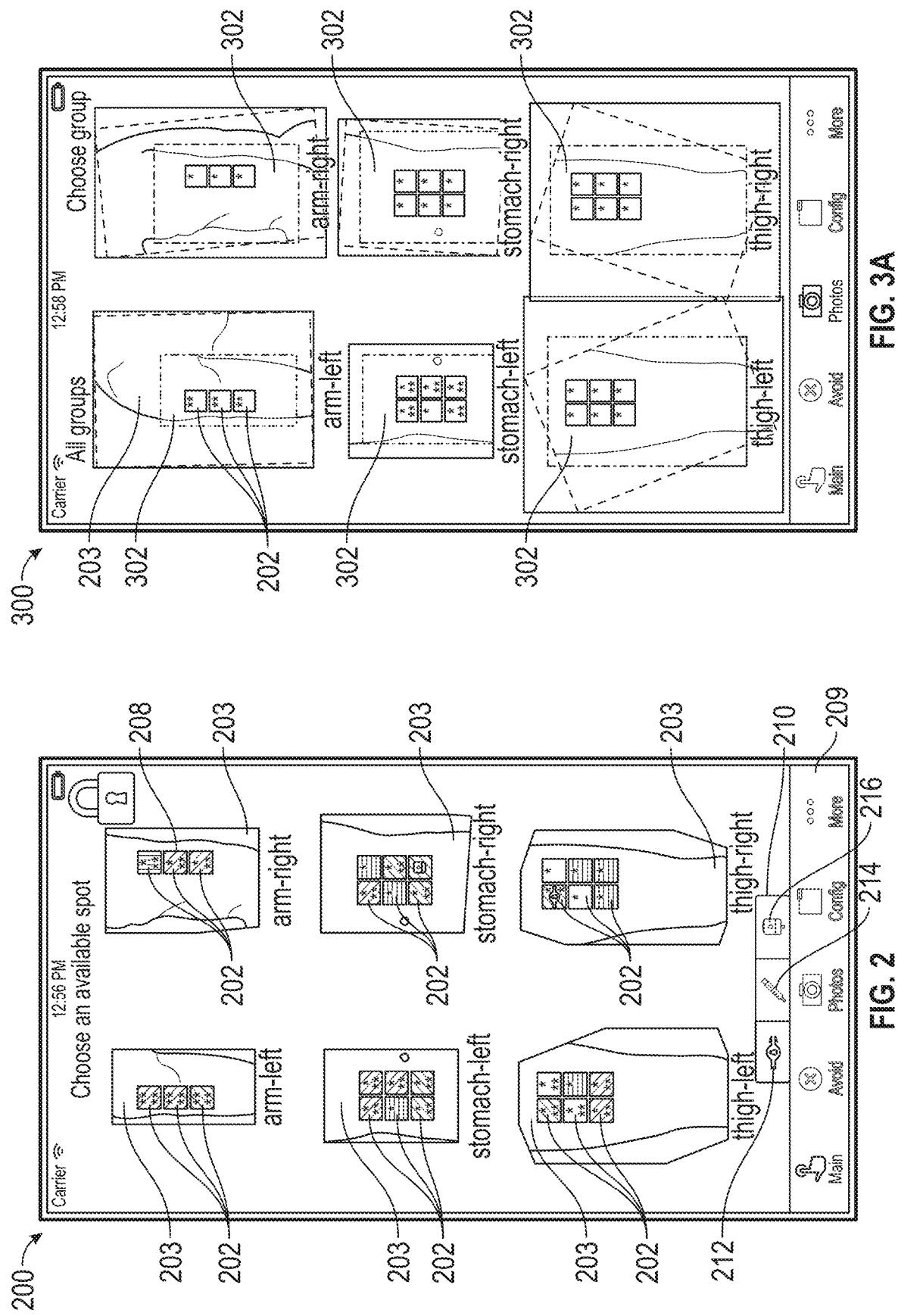
FIG. 2 illustrates an insulin rotation application running on a computing device, in accordance with various embodiments.
FIG. 3A illustrates an exemplary interface for creating or editing images, groups, or sites in an insulin rotation application, in accordance with various embodiments.

Referring now to FIG. 2, interface 200 of insulin rotation application 110 is shown displaying several sites 202 suitable for insulin administration or monitoring on body 106 (of FIG. 1A), in accordance with various embodiments. Each site 202 may by superimposed over an image 203 of a body part suitable for an insulin management device 102 (of FIG. 1A). Sites 202 may be visually represented by shapes 208 having visual indicators describing the status of sites 202. Shapes 208 may comprise squares, circles, hexagons, polygons, irregular shapes, drawn perimeters, or other boundaries defining a site 202 on image 203. Each site 202 defined on image 203 may correspond to a site 104 (of FIG. 1A) on body 106 (of FIG. 1A) suitable to receive an insulin management device 102. Visual indicators may comprise colors, numbers, patterns, symbols, shading, or other visual indicators suitable to convey the status of a site 202. Possible statuses of sites 202 include available for insulin management device 102, unavailable for insulin management device 102, recently used, adjacent a recently used site 202, used within a predetermined time interval, or other status relevant to rotating insulin administration and monitoring sites.

In various embodiments, the images 203 overlaid with sites 202 may assist users in orienting and positioning an insulin management device 102 (of FIG. 1A) on a body 106 (of FIG. 1A) at injection sites and/or blood draw sites corresponding to sites 202. Interface 200 may include locking functionality such that locking prevents users from incidentally interacting with interface 200. Interface 200 may also include a tab menu 209 to navigate to the various screens including the main screen shown in interface 200, an avoid screen, a photos screen, a configuration screen, or other interface screens for configuring or using insulin rotation application 110.

In various embodiments, interface 200 may also include a device menu 210 showing various insulin management devices 102 for selection. Insulin management devices 102 may be, for example, pump 212, syringe 214, and continuous glucose monitor 216. In that regard, types of use recorded by application 110 at a site 202 may correspond to insulin pumps, syringe injection, and glucose monitors.

In various embodiments, insulin rotation application 110 running on computing device 108 may operate in two stages of operation, including a configuration stage and a normal usage stage. Interface 200 may be used for normal usage with interface 300 with various other interfaces of insulin rotation application 110 used for manual configuration. The configuration setup may be satisfied using pre-made configurations available on a configuration management interface for rapid startup and transition to rotation management using insulin rotation application 110.

With reference to FIG. 3A and according to various embodiments, users may manually configure application 110 at least in part by using photo interface 300 to capture, upload, manipulate, rotate, crop, draw, or otherwise prepare images 203 (of FIG. 2) for overlaid sites 202 (also of FIG. 2) representative of sites 104 for insulin delivery or monitoring on body 106. Users may also create groups 302 of sites 202 representative of regions on body 106. For example, groups of sites 202 may be grouped by right arm, left arm, right stomach, left stomach, right thigh, left thigh, or any other region of body 106 suitable for insulin management device 102.

In various embodiments, a group 302 of sites 202 may also include image 203 with the sites 202 selectively overlaid on image 203. Group 302 may include varying numbers of sites 202, and each site 202 may represent an area on body 106 of half a square inch, one square inch, 4 square inches, or any other area suitable for rotation without causing overuse at any one site 104 on body 106. Photo interface 300 of insulin rotation application 110 may thus configure groups with photo overlays selectively locating sites 202 on image 203. Photo interface 300 may enable the user to manually adjust the configuration of sites 202. Adjustments to or configuration of sites 202 in group 302 may comprise altering the overlay position, size, number, underlying image 203, orientation, shape, or visual indicia of recent use.

In various embodiments, photo interface 300 may display all groups 302 created for an active profile. Photo interface 300 may also display menus to select a group 302 or a selected group 302 itself. Photo interface 300 may also facilitate movement of groups on photo interface 300 showing more than one group 302 so that groups 302 are arranged in a desirable manner in insulin rotation application 110. For example, photo interface 300 may support a drag-and-drop interaction to move groups 302 into position relative to one another or relative to photo interface 300.

In various embodiments, photo interface 300 may display the groups 302 of sites 202 for adjustment and may also facilitate creation of new groups 302 through menu 312, in accordance with various embodiments. Photo interface 300 may also enable users to show all groups 302 and select a single group 302 to edit. Photo interface 300 may also create new groups.

With reference to FIG. 3B and continuing reference to FIG. 3A, users may select "Choose group" or an icon or link having similar functionality as shown in the upper-right corner of photo interface 300 to launch a menu 312 with a "Create a new group" option along with selection options for each existing group.

With reference to FIG. 3C and continuing reference to FIG. 3A, group editing interface 320 is shown for editing a single group 302 using menu 322, in accordance with various embodiments. Group editing interface 310 may launch in response to a user selecting a particular group or selecting 'Create a new group' from menu 312. Group editing interface 310 may create or edit a group name, choose or create an image 203, alter an image 203, modify or add sites 202 to group 302, or otherwise edit a group 302.

In various embodiments and with reference to FIG. 3D, a user may select 'Create a new group' or an icon or link having similar functionality from menu 312 (of FIG. 3B) to launch a group creation interface 330. Group creation interface 330 will accept a name in text. An example of a default name is 'newgroup,' though any default name may be used. A user should select a descriptive group name for ease of usability. The new name should be different from the other existing group names, which may be shown in group creation interface 330 (e.g., in the list to the right). Group creation interface 330 may turn red and highlight the group name in the list in response to a group name being duplicative of an existing group. Group creation interface 330 may force users to change the group name until the new group name is unique.

In various embodiments, group creation interface may also determine how many rows and/or columns of sites are present in a group 302. A user may select the desired number of rows and columns based on the size of the body 106 (of FIG. 1A), for example, or based on the size of the area of the body 106 where sites 104 (of FIG. 1A) represented by sites 202 (of FIG. 2) in group 302 (of FIG. 2) are located. Sites 202 may also be shaped based on selections from group creation interface 330. Site shapes may include, for example, squares, circles, hexagons, polygons, irregular shapes, drawn perimeters, or other boundaries defining a site 202 (of FIG. 2) on image 203 (of FIG. 2).

Referring to FIG. 3E and with brief reference to FIG. 3C, a photo overlay for a group 302 may be created by selecting an image 203 in response to selecting 'Choose or create a photo . . .' or an icon or link having similar functionality to launch photo selection interface 340. Photo selection interface 340 may select an image 203 for group 302 in response to user input. Image 203 may be chosen from several sources such as the App directory, iCloud, cloud storage, network storage, local storage, or electronic communication channels such as SMS, iMessage, or email. The camera on device 108 may also capture a photograph suitable for use as image 203 in real time.

In various embodiments, a user may tap on the desired group 302 in group editing interface 310 (of FIG. 3B) to choose image 203 for group 302 using a touchscreen interface on device 108 (of FIG. 1A). Insulin rotation application 110 may enter a group editing mode in response to the selection. The user may tap on the group again to bring up the photo selection interface 340. The user may tap 'Choose or create a photo . . .' in menu 322 (of FIG. 3C), which may launch photo selection interface 340. Menu 342 of photo selection interface 340 may include options to choose or create a photo with the camera, from the App directory, from the Photo library, or from the iCloud or other remote storage location. If group 302 already has a photo, then choosing a new photograph may replace the previously selected photograph.

In various embodiments, a user may choose 'Camera' to launch a camera application running on device 108 to operate a camera integrated into device 108 (of FIG. 1A). The user may capture an image and use the image or elect to recapture a new image. The new image 203 may automatically be underlaid behind the group 302 of sites 202. Images may also be drawn using an integrated drawing application running on device 108.

In various embodiments, a user may choose 'App directory' to launch a directory operated by insulin rotation application 110. The directory may retain photos used by insulin rotation application 110 presently or in the past. When loading image 203 from a remote location such as the cloud, insulin rotation application 110 may copy the image 203 into the directory.

In various embodiments, image 203 may be edited after being selected using photo selection interface 340. Insulin rotation application may support common editing functions to manipulate image 203 such as, for example, black and white conversion. Displaying image 203 in black and white or greyscale may create contrast between sites 202 with color coding and the underlaid image 203. Another example of an image manipulation function may include reflecting an image vertically or horizontally so a photo of a right arm can be used as a left arm.

In various embodiments, image 203 may be shifted, scaled, and rotated to give view of the context around the sites 202 suitable for use in insulin rotation application 110. Image 203 may further have a mask positioned to selectively expose a portion of the image 203 and exclude undesired elements. For example, an Image button may be selectable in an interface of insulin rotation application 110 to enable users to drag, zoom, and rotate with finger gestures. These image manipulation techniques may make sites 202 representative of sites 104 that are approximately 1 square inch, 2 square inches, 3 square inches, 4 square inches, 5 square inches, or another suitable area to support site rotation. As used herein in reference to surface area, approximately may mean +/−5%, +/−10%, +/−15%, +/−20%, +/−25%, or +/−30%.

In another example of image manipulation supported by insulin rotation application 110, a Mask button may be selectable in an interface of insulin rotation application 110 to apply and adjust a mask over image 203. A mask may be a window that selects part of image 203 to show while cropping out the unselected portion of image 203. A mask may enable users to selectively display a desired portion of image 203 while hiding the remainder of image 203. A user may drag and zoom the mask to select the part of the photo in response to tapping the Mask button displayed on device 108 running insulin rotation application 110.

With reference to FIG. 3F, site editing interface 350 of insulin rotation application 110 is shown, in accordance with various embodiments. Site editing interface 350 may launch in response to an input on menu 322 selecting edit sites or a similar menu entry. Site editing interface 350 may support adding sites 202 to groups 302, selecting sites 202 for editing, deleting sites 202 from groups 302, moving sites 202 within groups 302, dividing a single group 302 into two or more groups 302, or merging multiple groups 302 into a single group 302.

In various embodiments, insulin rotation application 110 may support alternative mechanisms to set the scale of sites 202 and images 203. For example, insulin rotation application 110 may set the spot size in a settings screen and set the image size in a photo editing screen. Site 202 grids may then have a fixed size relative to the photo. Shifting and rotating the image may enable site manipulation without resizing the image in some embodiments. Insulin rotation application 110 may also support 3-dimensional touch adjustments to mark the perimeter of groups of spots.

In various embodiments, insulin rotation application 110 may include a 3-dimensional representation of a body model. The 3-dimensional model may support rotation and zoom functions for convenient viewing. Insulin rotation application 110 may include several default 3-dimensional models or mutable 3-dimensional models to accurately depict a patient based on selections or entries of gender, age, body composition, height, weight, or other factors suitable to accurately represent a human. Groups 302 of sites 202 may be overlaid on various areas of the 3-dimensional model representative of the user's body. Images of the body region modeled on the 3-dimensional model may be generated automatically in response to positions of sites 202. Images 203 may be automatically selected and adjusted without manual image manipulation. Insulin rotation application 110 may change between 2-dimensional images 203 and the 3-dimensional model to facilitate site 202 orientation for insulin infusion pumps and other devices.

Referring now to FIG. 4, configuration of insulin rotation application 110 may also include setting timing and area parameters such as, for example, recent parameters 402 and near parameters 404 for each type of insulin management device 102 (of FIG. 1A) using settings interface 400. Other types of parameters relevant to placement of each type of insulin management device 102 may also be set during configuration. In that regard, pump 212, syringe 214, and continuous glucose monitor 216 may each have a recent parameter 402 and a near parameter 404 having different values. Recent parameter 402 may correspond to the amount of time a site 202 is unavailable for reuse after the site 202 has been used. A site 202 may become available for use again after a duration greater than the period set in the recent parameter 402 has passed. Near parameter 404 may correspond to the amount of time a spot is unavailable after an adjacent spot has been used. Duration parameter 406 may correspond to the recommended amount of time continuous glucose monitor 216 should stay in place. Insulin rotation application 110 may suggest moving a continuous glucose monitor 216 in response to a duration greater than the time set in duration parameter 406 has passed. For example and with brief reference to FIG. 5D, the icon at site 502 indicating an active glucose monitor in interface 500 may change colors, include an x-out, flash, or otherwise give a visual indicator reflecting movement or removal is overdue in response to the glucose monitor remaining in place longer than the duration parameter.

In another example and referring again to the parameter values and interface 400 depicted in FIG. 4, site 202 may not be reused for at least 72 hours (3 days) in response to a syringe being used at site 202. Similarly, site 202 may not be reused for at least 15 days in response to a pump being used at site 202. Varying rotation and adjacency limitations for each type of insulin management device 102 enables insulin rotation application 110 to account for a syringe being used just once at site 202 and thus causing less damage to the site 202 than would be caused by a pump, which stays in place for 2-3 days, being used at site 202. The pump and monitor parameters may thus be measured in days, and the syringe parameters may be measured in hours to reflect the different demands of each insulin management device 102 on a site 202.

In various embodiments, site 202 may become unavailable in response to being used for an insulin management device 102. Insulin rotation application 110 may not permit usage of a site again until a time period at least as long as recent parameter 402 passes for the device type last used at site 202. Near parameter 404 corresponds to the time period any adjacent site 202 is made unavailable by insulin rotation application 110 in response to using site 202 for an insulin management device 102.

In various embodiments, interfaces in insulin rotation application 110 may include a child lock. The child lock may force heightened authentication before unlocking insulin rotation application 110. A child or third-party with limited authorization to use device 108 (of FIG. 1A) may be restricted from accessing some or all interfaces in insulin rotation application 110. Interfaces may be available in response to entry of privileged credentials or privileged biometric input.

Referring now to FIG. 5A, site selection interface 500 is shown having group 302 with all sites 202 available for use, in accordance with various embodiments. Sites 202 may have visual indicators regarding availability of the site to accept an insulin management device 102 (of FIG. 1A). For example, FIG. 5A depicts six sites 202 available on the right thigh by shading sites 202 a predetermined or preselected color. The shading may be any color, cross hatching, greyscale, pattern, icons, or other visual representation to indicate sites 202 are available for use.

Referring to FIG. 5B, site selection interface 500 is shown having site 502 in use and thus having a different shading or visual indicator than available site 503 shown in FIG. 5A. The icon depicted in site 502 may indicate the site is currently in use by a pump 212. Adjacent site 504 and site 506 may each be shaded a different color or otherwise indicate unavailability due to being adjacent to site 502, which was recently used or is currently in use. Sites 504 and 506 have near status and may be unavailable even though the sites may not have been selected directly. In response to recent parameter 402 (of FIG. 4) being set at 15 days and near parameter 404 (of FIG. 4) being set at 7 days for an insulin pump set in settings interface 400 (of FIG. 4), for example, site 502 may not be used for insulin again for at least 15 days and sites 504 and 506 may not be used for insulin again for at least 7 days after pump use.

For example, all sites 202 in selection interface 500 of FIG. 5A are depicted as available for selection using a visual indicator selected or defaulted in visual indicator interface 600 (of FIG. 6). Application 110 may unlock the screen in response to a tap on the lock icon in the upper-right corner of selection interface 500. An insulin management device 102 may be selected in device menu 210.

Continuing the above example and changing reference from FIG. 5A to FIG. 5B, application 110 may change the visual indicator in site 502 from "available" status to "newly selected" status in response to detecting a touch on the site 502 via a touch screen of device 108 (of FIG. 1A). The device depicted in the "newly selected" status indicator may correspond to the device selected in device menu 210. Sites 504 and 506 may show the visual indicator indicating "near" status in response to the sites 202 being adjacent to the chosen site 502.

In various embodiments, a site 502 may become unavailable for a time to enforce a resting period in response to the site being used for insulin to allow the site 202 to recover from the insulin infusion. In addition, any adjacent sites 504 and 506 may also become unavailable for a time to rest the general area. Making adjacent sites unavailable creates a buffer zone around the selected spot to nullify the impact of inaccurate insulin management device 102 placement.

Figure 5D:
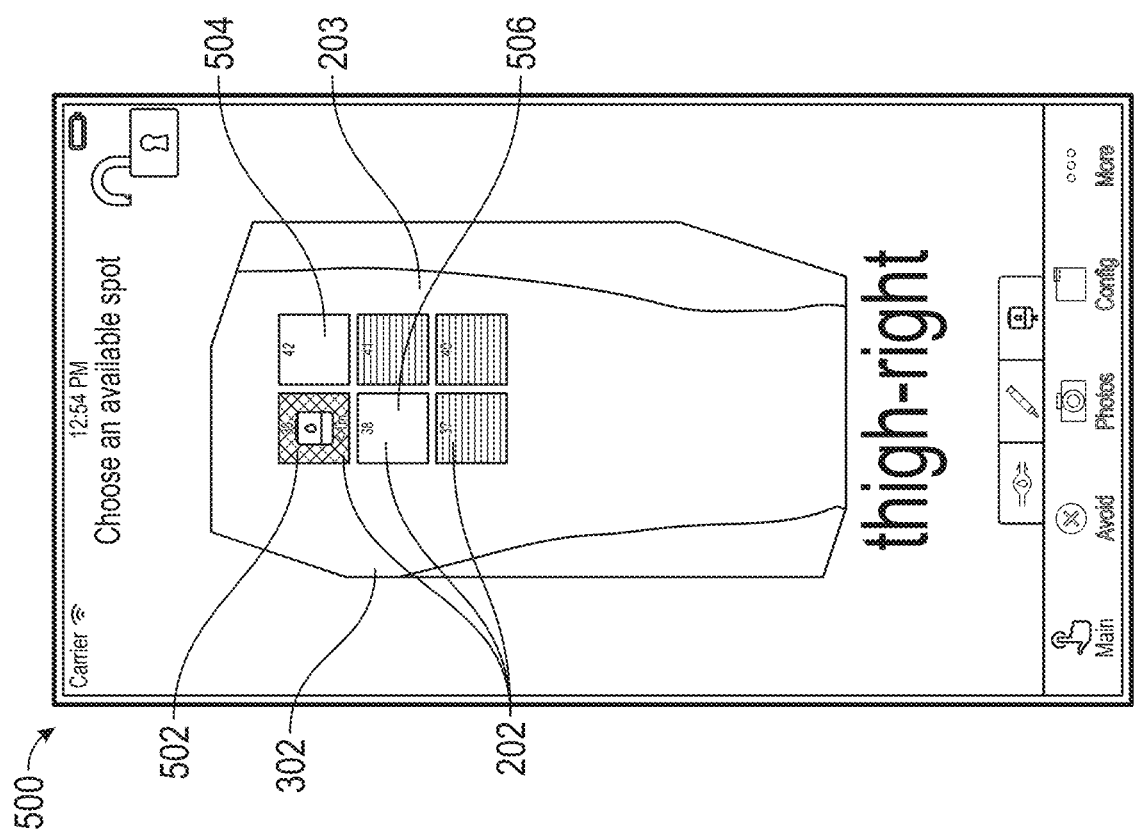
FIG. 5D illustrates a group of insulin administration sites overlaid on an image of a body part with one of the sites newly selected for use by a glucose monitor, in accordance with various embodiments.
Figure 5C:
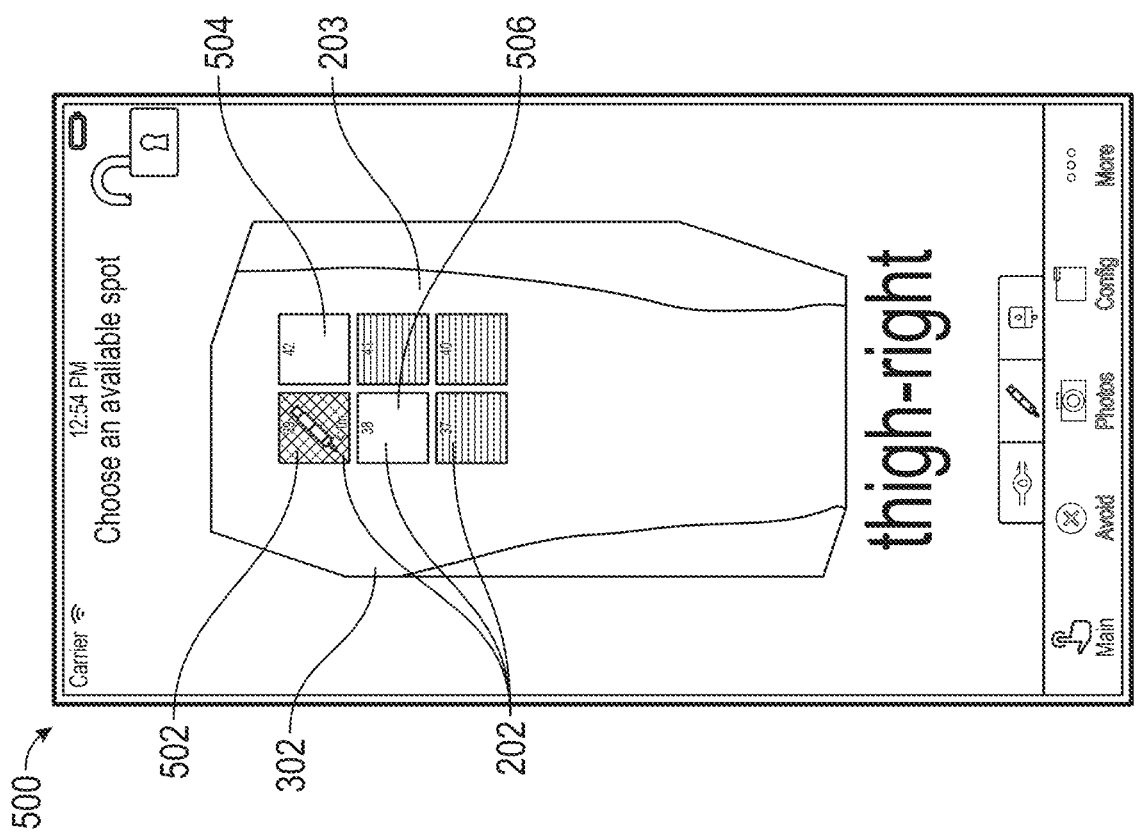
FIG. 5C illustrates a group of insulin administration sites overlaid on an image of a body part with one of the sites newly selected for use by a syringe, in accordance with various embodiments.

Referring now to FIG. 5C, site selection interface 500 is shown having site 502 in use and thus having a different shading or visual indicator than available site 503 shown in FIG. 5A or 5B. The visual indicator in FIG. 5C depicts a syringe to indicate site 502 was recently used with a syringe. Adjacent sites 504 and 506 may each be shaded a different color or otherwise indicate unavailability due to being adjacent to site 502, which was recently used or is currently in use. Sites 504 and 506 have near status and may be unavailable even though they have not been chosen directly. In response to recent parameter 402 (of FIG. 4) for a syringe being set at 72 hours and near parameter 404 (of FIG. 4)

being set at 12 hours in settings interface 400 (of FIG. 4), for example, site 502 may not be used for insulin again for at least 72 hours and sites 504 and 506 may not be used for insulin again for at least 12 hours after syringe use.

Referring now to FIG. 5D, site selection interface 500 is shown having site 502 in use and thus having a different shading or visual indicator than available site 503 shown in FIGS. 5A, 5B, and 5C. The visual indicator in FIG. 5D depicts a glucose monitor to indicate site 502 was recently used or is in use with a glucose monitor. Adjacent sites 504 and 506 may each be shaded a different color or otherwise indicate unavailability due to being adjacent to site 502, which was recently used or is currently in use. Sites 504 and 502 have near status and may be unavailable even though they haven't been chosen directly. In response to recent parameter 402 (of FIG. 4) for a glucose monitor being set at 90 days and near parameter 404 (of FIG. 4) being set at 21 days in settings interface 400 (of FIG. 4), for example, site 502 may not be used for insulin management device 102 (of FIG. 1A) again for at least 90 days and sites 504 and 506 may not be used for insulin management device 102 (of FIG. 1A) again for at least 21 days after glucose monitor use.

Referring again to FIG. 2, interface 200 may display the layout of sites 202 in groups 302, in accordance with various embodiments. The sites 202 may be coded to indicate status. Interface 200 may accept input to select a site 202 for pump placement, injection, or glucose monitoring. Interface 200 may be locked and unlocked using a button or touch interface to prevent accidental changes.

In various embodiments, a user may select insulin management device 102 (e.g., pump 212, syringe 214, or continuous glucose monitor 216) for placement in response to a suggestion or status from application 110. Application 110 may include sites 202 that are either available or unavailable for placement of insulin management device 102. Sites 202 may be unavailable in response to being recently used, being adjacent to a recently used site 202, being labeled as a site 202 to avoid, or other suitable criteria. Users may not select unavailable sites 202 unless the user overrides insulin rotation application 110 (as described below with reference to FIG. 5E). Application 110 may color code unavailable sites 202 to differentiate unavailable sites 202 from available sites 202.

In various embodiments, application 110 may make available for selection sites 202 that are not otherwise unavailable as described above. Application 110 may color code or use patterns, icons, or other visual indicators to differentiate available sites 202 from unavailable sites 202. Available sites 202 may also be categorized. For example, application 110 may identify a best available site 202 in response to a site 202 being an available spot unused for a duration greater than a predetermined threshold. Application 110 may also identify a best available site in response to a site 202 having a duration of rest greater than other sites. Available sites 202 may be selected in response to a user input. Application 110 may recommend that users choose a best spot when available to promote uniformity of spot usage over time.

In various embodiments, application 110 may also categorize sites 202 as new. Site 202 may be new in response to being selected. A new site 202 may be deselected in response to an erroneous selection or other change. Site 202 may remain in a new state for a predetermined duration. For example, a site 202 may remain in a new state for 1 minute, 5 minutes, 10 minutes, 20 minutes, 30 minutes, an hour, or other suitable duration to allow status change in response to erroneous selection or a user desire to change a selection. Application 110 may change the site status to unavailable in response to the site 202 being recently used and expiration of the predetermined duration for new categorization.

With reference to FIG. 5E, an override interface 510 is shown, in accordance with various embodiments. Override interface 510 may capture a reason for selection of a site 202 marked unavailable. Override interface 510 may comprise menu 512 with prepopulated override justifications 514 for selection. Override interface 510 may include a free text field 516 to capture a justification for selection of an unavailable site 202. Overrides may be reviewed by an attending physician, diabetic educators, nurses, caretakers, or patients and may reveal usage patterns specific to the patient.

Now referring to FIG. 6 and with continuing reference to FIG. 2, sites 202 may be visually coded to indicate the status of the site 202 as determined in visual indicator interface 600. The colors, patterns, icons, or other visual indicators used by application 110 to visually distinguish between categorizations for site 202 may be selectable by a user in themes or groupings or may be customizable by a user in visual indicator interface 600. In that regard, application 110 may determine the palette or grouping of visual indicators in response to receiving a user input.

In various embodiments, visual indicator interface 600 may include selectable visual indicators for each category of site 202. The visual indicators selected in visual indicator interface 600 may be used in interface 200 to distinguish between possible states of sites 202. Categories for sites 202 may include various unavailable categories including recently used, spots to avoid, adjacent a recently used spot, newly selected, or other unavailable categories. Available categories may include available or oldest available, for example. Users may select a grouping of visual indicators by selecting an indicator grouping 602 in visual indicator interface 600.

With reference to FIG. 2, application 110 may identify a type of insulin management device 102 using device menu 210 of interface 200 before selecting a site 202. Application 110 may also default the device type in device menu 210 to one of pump 212, syringe 214, and continuous glucose monitor 216. Application 110 may then change a visual indicator for a site 202 in interface 200 in response to an input indicating selection of the site 202. For example, application 110 may change the visual indicator on a site 202 to reflect the categorization changing from "available" to "new." Application 110 may depict the device type chosen from the device menu 210 in site 202 in response to site 202 being selected. The change in visual indicator may reflect the updated status of site 202 using the visual indicator selected or defaulted in visual indicator interface 600. Application 110 may thus present visual feedback confirming the selection. An input indicating selection of an unavailable site 202 may not result in a changed visual indicator.

In various embodiments, application 110 may undo a selection of site 202 in response to an input selecting the same site 202 again or selecting a different available site 202. Application 110 may support deselection of a site 202 for a predetermined duration. Application 110 may thus undo a selection in response to an error or a changed decision on where to place insulin management device 102. A newly selected site 202 may retain a "new" status for the predetermined duration to allow change of selection. Application 110 may change the visual indicator of site 202 in response to the predetermined duration for deselection of a site 202 expiring without an input triggering deselection. Status for a site 202 may not be directly modifiable by a user in various embodiments.

With reference to FIG. 7A, application 110 may create an entry in the history log 702 reflected in history interface 700, in accordance with various embodiments. Application 110 may support editing in history interface 700. History interface 700 lists site selections recorded in history log 702. Application 110 may modify history log 702 in response to user input deleting, creating, or changing a log entry. For example, application 110 may delete history items and/or even clear history log 702 in response to a user input on link 708 to remove rows by tapping a touch screen interface of device 108 (of FIG. 1A) and selecting rows for deletion. Application 110 may clear history log 702 in response to an input selecting a 'Clear history' button or link. Log entries 703 may include a device type 704, group and site description 706, a timestamp, and other data related to an individual use of insulin management device 102 (of FIG. 1) at a site 202 (of FIG. 2). Log entries 703 may include a justification 709 entered into override interface 510 (of FIG. 5E) for reusing a site 202 categorized as unavailable before the recent or near durations set in settings interface 400 (of FIG. 4) have lapsed.

In various embodiments, application 110 may modify the device type, date, or time of an entry in history log 702. Referring now to FIG. 7B, history modification screen 710 may enable input regarding device type, time, date, group, site, early use justification, or identifier for site 202 used. Application 110 may detect user inputs to trigger updates to history log 702. Updates may correct user errors, bugs in application 110, or other inconsistencies to synchronize history log with deployment of insulin management device 102 at a site 104 on body 106 (all of FIG. 1A).

Figure 8:
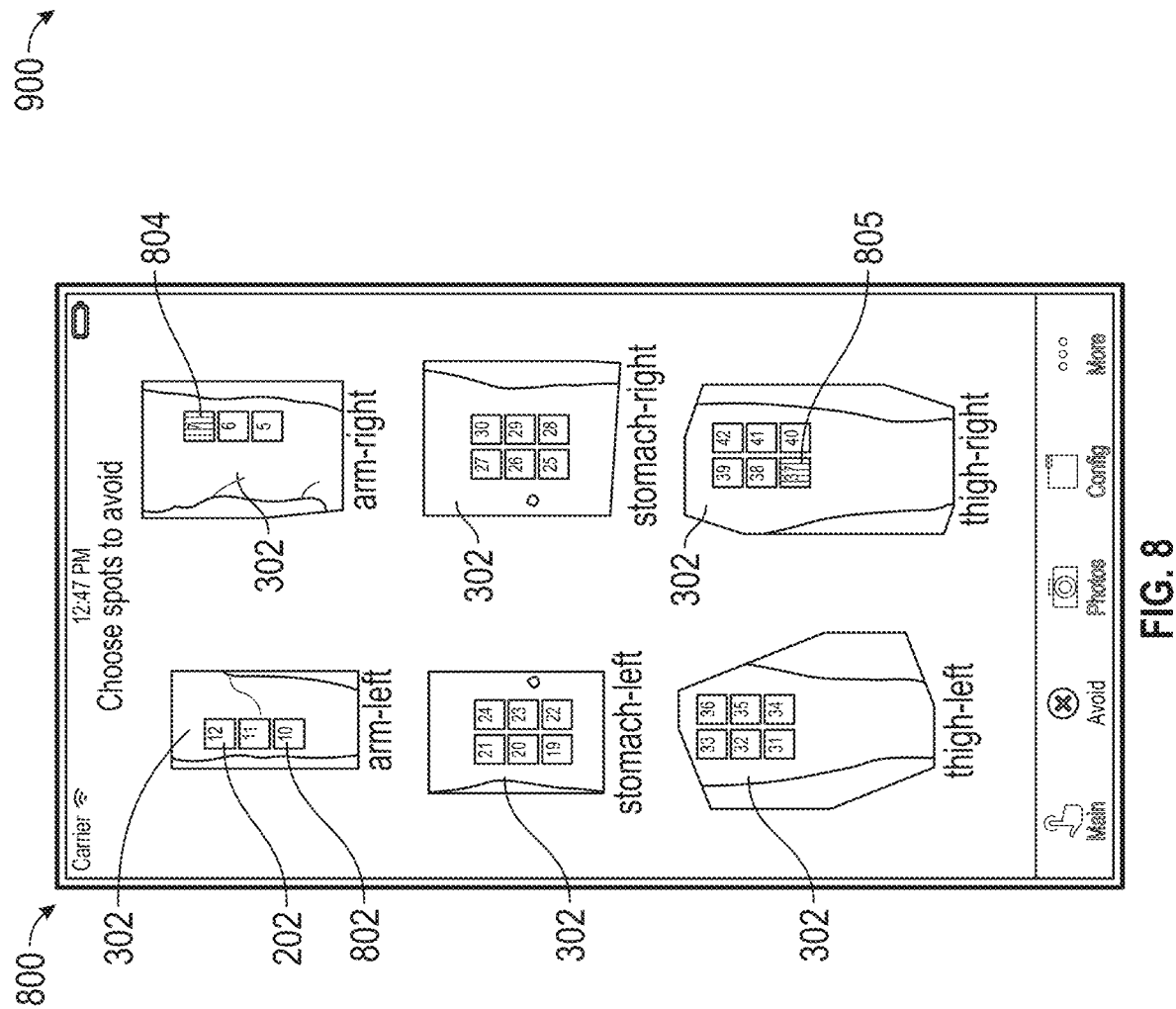
FIG. 8 illustrates an exemplary interface for selecting potential insulin administration sites to avoid on a body, in accordance with various embodiments.

Referring to FIG. 8, application 110 may store sites 202 to avoid in response to input from a user in avoidance interface 800. Avoidance interface 800 may support selection of spots to avoid in response to users clicking on or tapping sites 202 using an input to device 108 (of FIG. 1A). For example, site 802 unselected for avoidance from sites 202 in groups 302 may have a visual indicator showing the sites may be considered by application 110 for selection. Site 804 and site 805 selected in avoidance interface 800 may have a visual indicator showing sites 804 and 805 are selected for avoidance by application 110. Sites 804 and 805 selected for avoidance by application 110 may not be chosen by a user for placement of insulin management device 102. Users may identify sites 202 that are injured or sensitive in avoidance interface 800.

Figure 9:
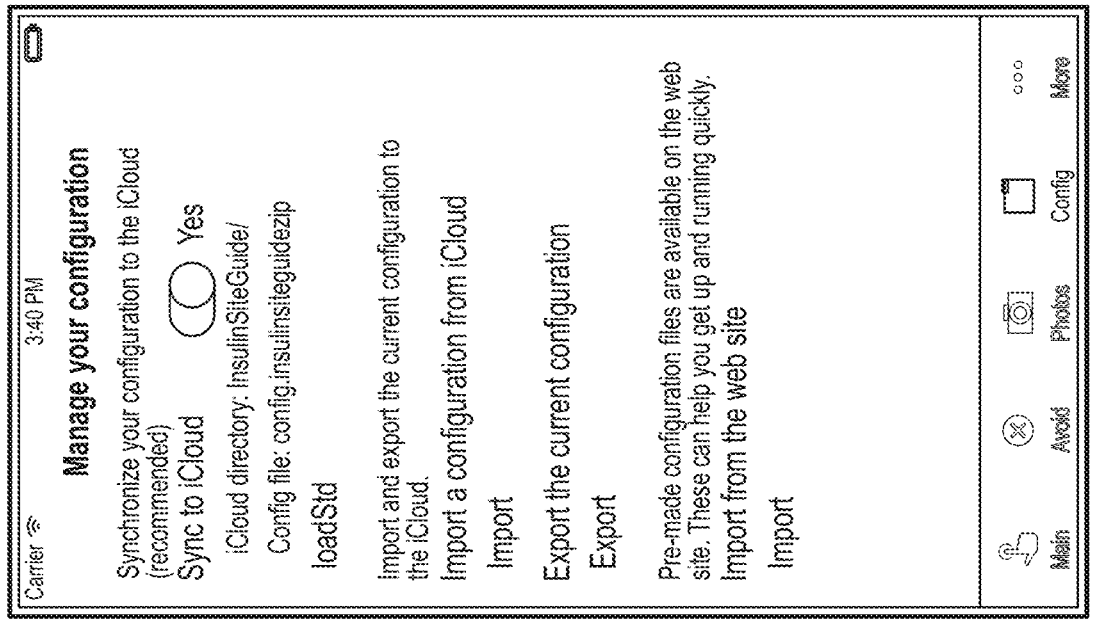
FIG. 9 illustrates an exemplary interface for managing a configuration file for an insulin rotation application, in accordance with various embodiments.

With reference to FIG. 9, configuration interface 900 of application 110 (of FIG. 1A) is shown, in accordance with various embodiments. Configuration interface 900 may manage the state of application 110 by editing state variables stored in a configuration file. The configuration file may contain application data such as history log 702, state data, images, settings, visual indicator selections, group 302 (of FIG. 3A) data, site 202 (of FIG. 2) data, variables selected or defaulted in the interfaces described herein, or other data to configure application 110 for operation. Application 110 may write the configuration file to storage 174 locally on device 108 and/or remotely.

In various embodiments, writing the configuration file may save any changes, updates, history, or selections made in application 110. Application 110 may thus load default configurations with predetermined groups 302, sites 202, images 203, history log 702, and other variables or settings to start application 110 in a usable state. In that regard and referring briefly to FIG. 1A, different devices 108 running application 110 may save state data in a configuration file by writing to a remote or remote storage 112. Devices 108 may sync application data by reading and/or writing the configuration file to a mutually accessible location. A treating physician may thus access application 110 for a patient to monitor a patient by retrieving updated data (e.g., updated history log 702) on site rotation for the patient. Application 110 running on different devices 108 may have different read/write permissions to facilitate error free status sharing between devices.

Figure 10:
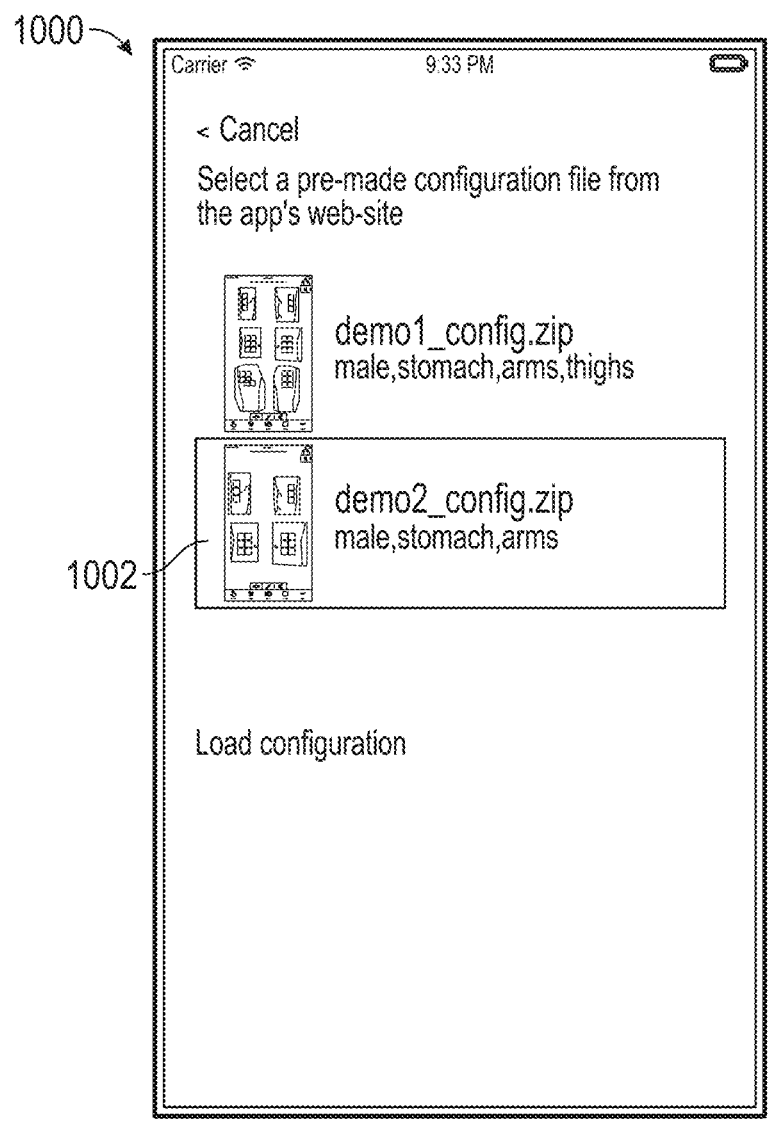
FIG. 10 illustrates an exemplary interface for selecting a configuration file for an insulin rotation application, in accordance with various embodiments.

With reference to FIG. 10, an import interface 1000 is shown for importing a default configuration file to application 110, in accordance with various embodiments. Application 110 may access a remotely hosted website or data repository offering a selection of premade configuration files. The premade configuration files may be imported directly into application 110. Each configuration file may contain premade groups 302 (of FIG. 3A) of sites 202 (of FIG. 3A) with corresponding images 203 (of FIG. 3A). Premade groups 302 may include various body parts such as, for example, stomach, left arm, right arm, left thigh, right thigh, or other suitable locations for insulin management device 102 (of FIG. 1A). Premade configuration files may also be made for adult females, adult males, young females, young males, and other suitable groupings that take into consideration average body area available for sites 202 of an appropriate size to manage insulin rotation. The history log 702 may be empty in a default configuration file. Users may selectively input adjustments into application 110 to customize the interfaces described herein.

In various embodiments, application 110 may select a default configuration in response to detecting a user input on import interface 1000. For example, a user may tap an import button to launch import interface 1000 and tap a premade configuration 1002. The user may then tap the "Load configuration" button to import premade configuration 1002.

In various embodiments, application 110 may export a configuration file in response to detecting a user selecting an "Export" button in configuration interface 900. Device 108 (of FIG. 1A) may communicate over network 114 (of FIG. 1A) to access remote storage 112 such as, for example, a cloud storage provider. Application 110 may select a directory in remote storage 112 that is available to write a configuration file. A device 108 running application 110 with access to remote storage 112 may then import a previously saved configuration file from remote storage 112.

In various embodiments, insulin rotation application 110 may support a multi-user mode. Multi-user mode may enable management of data for multiple diabetic patients. Insulin rotation application 110 may include an interface for adding and deleting diabetic patients. The interface may also allow the user (e.g., a physician or caretaker) to switch between the diabetic patients. Insulin rotation application 110 may include an image of each user to clearly indicate the selected patient. Insulin rotation application 110 may include a configuration file for each patient having a distinct name. A parent may thus manage site rotation for several diabetic children on a single device 108. A caregiver may manage site rotation for several diabetic patients on a single device 108.

Figure 11:
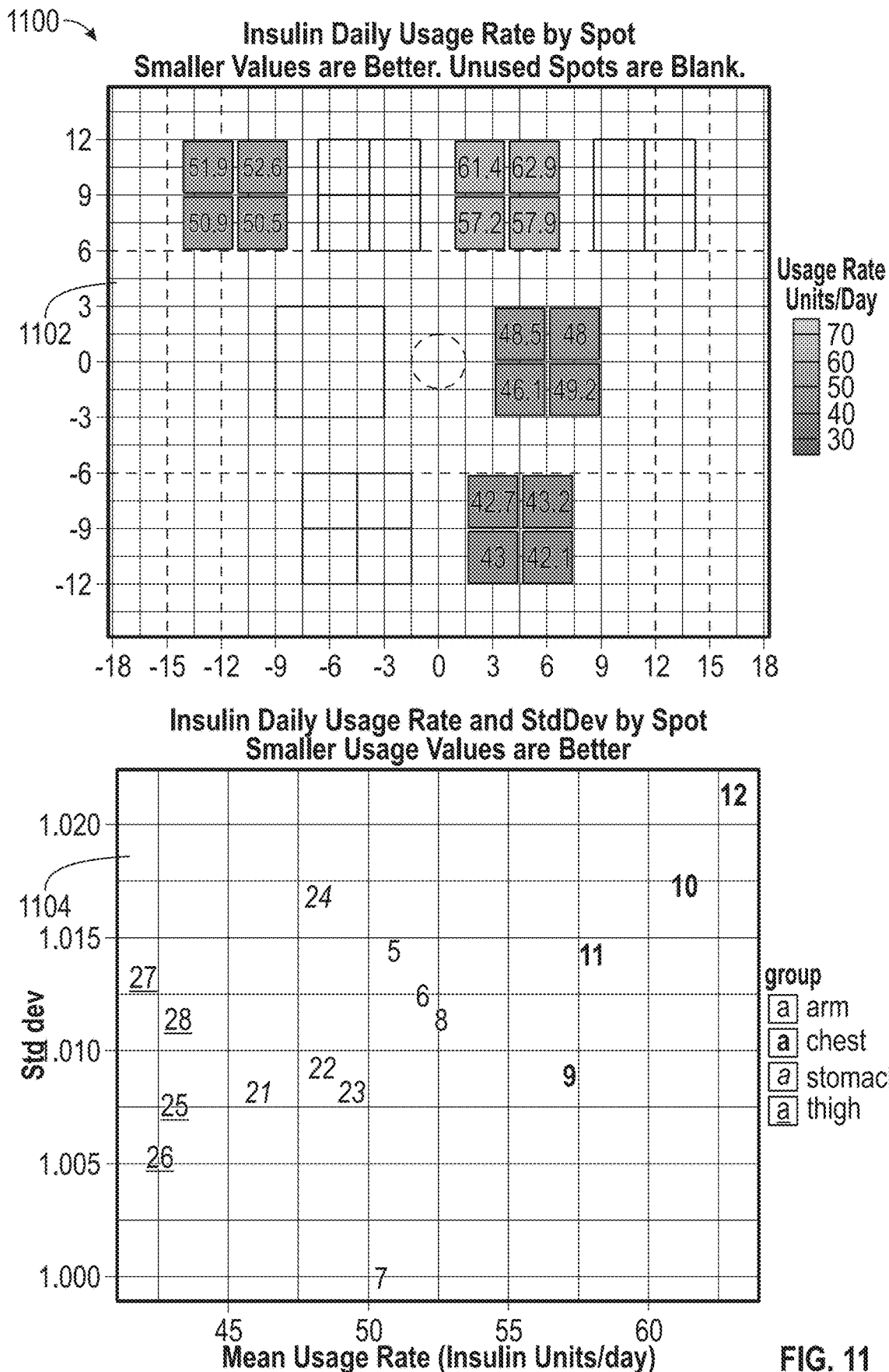
FIG. 11 illustrates an exemplary interface for assessing insulin usage rates at various insulin administration sites, in accordance with various embodiments.

Referring now to FIG. 11, usage interface 1100 is shown for tracking insulin usage at a given site 202 (of FIG. 1) over time. Usage interface 1100 may track daily usage rates at sites 202 as shown in chart 1102 and chart 1104. Chart 1102 and chart 1104 may integrate site rotation data from application 110 with insulin usage data, exercise data, carbohydrate data, and other suitable date to estimate insulin diffusion sensitivity of various sites 202. For example, an insulin management device may generate closed-loop or semi-closed-loop data used by insulin rotation application 110 for predictive modeling or statistical analysis. Lower insulin usage per day may show that a site 202 is better suited to absorb insulin. Higher insulin usage per day may show that a site 202 is injured or less suited to absorb insulin.

In various embodiments, system 100 may use a calculated insulin diffusion sensitivity to estimate site-specific insulin-on-board values. Site-specific insulin-on-board values may be used to integrate into closed-loop glucose control algorithms for developing a fully integrated Artificial Pancreas Device System (APDS). Calculated insulin diffusion sensitivity values and estimated site-specific insulin-on-board values may be integrated into closed-loop glucose control algorithms for fully integrated APDS.

Figure 12A:
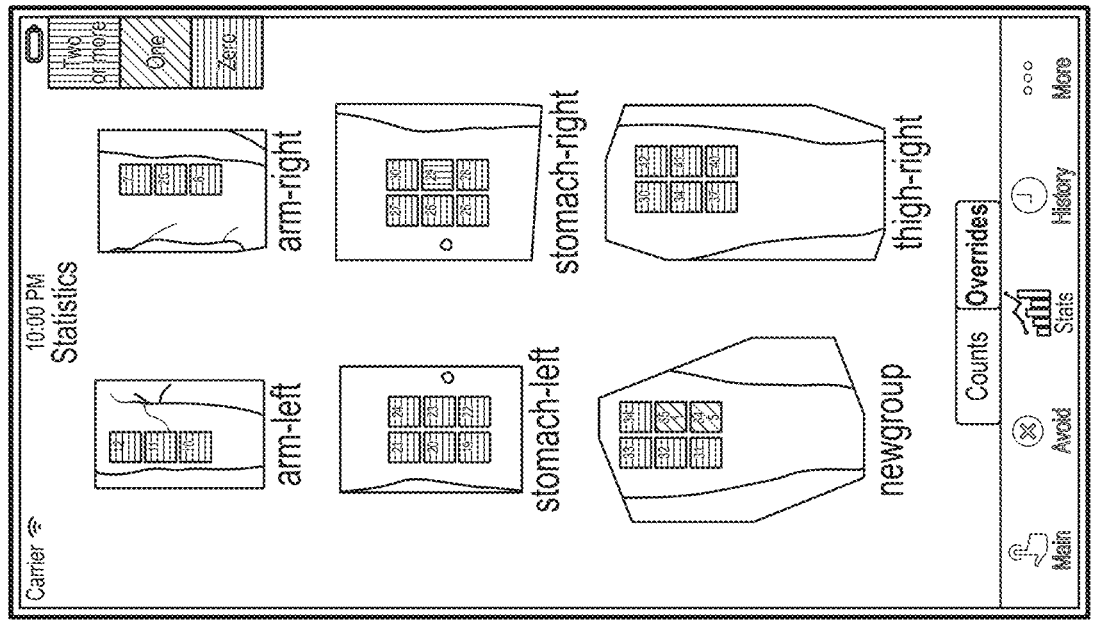
FIG. 12A illustrates an exemplary interface for tracking site usage over time, in accordance with various embodiments.

With reference to FIG. 12A, statistics interface 1200 is shown, in accordance with various embodiments. Statistics interface 1200 displays site usage counts. The "counts" mode of statistics interface 1200 tracks the number of times each site 202 has been used. Users may refer to statistics interface 1200 to balance usage of sites 202. Color coding may highlight sites 202 that are overused (e.g., in red) and underused (e.g., in blue). The user, a caretaker, a parent, or other person using insulin rotation application 110 may reference statistics interface 1200 to quickly assess an individual's rotation habits. Statistics interface 1200 may, for example, highlight the top 10% of most frequently used sites in red and the bottom 10% of least frequently used sites in blue. Other statistical thresholds may be preselected, predetermined, or entered to adapt statistics interface 1200 to a particular user's selection habits. Statistics interface 1200 may also use standard deviation, a predetermined count deviation, a deviation in duration since last use at each site, or other statistical approach to assessing site rotation habits.

Figure 12B:
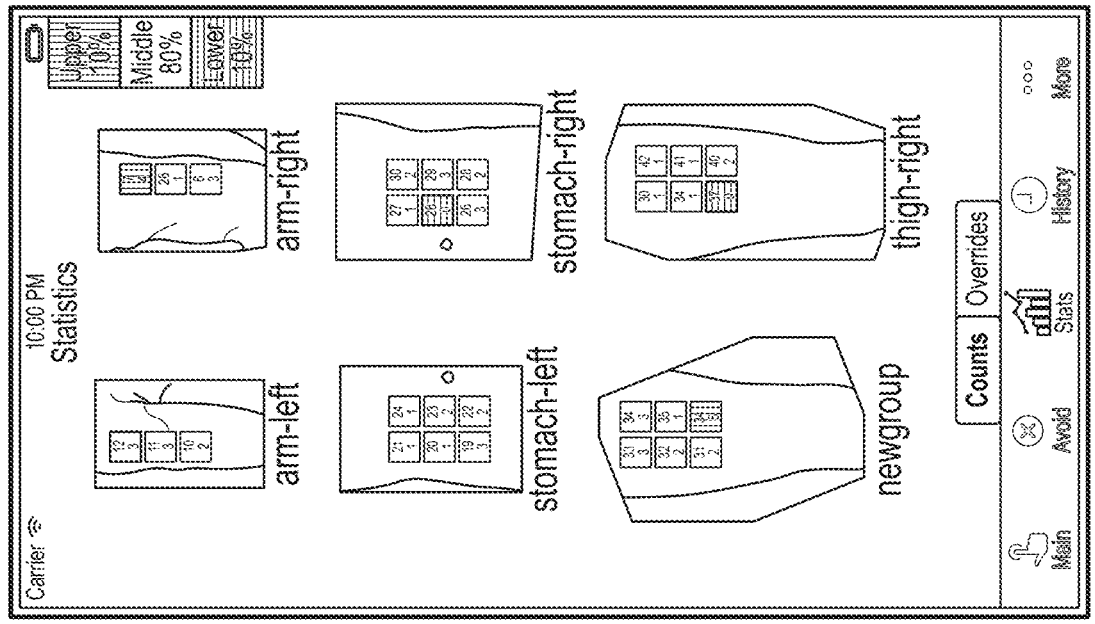
FIG. 12B illustrates an exemplary interface for tracking override usage at unavailable sites, in accordance with various embodiments.
Figure 12C:
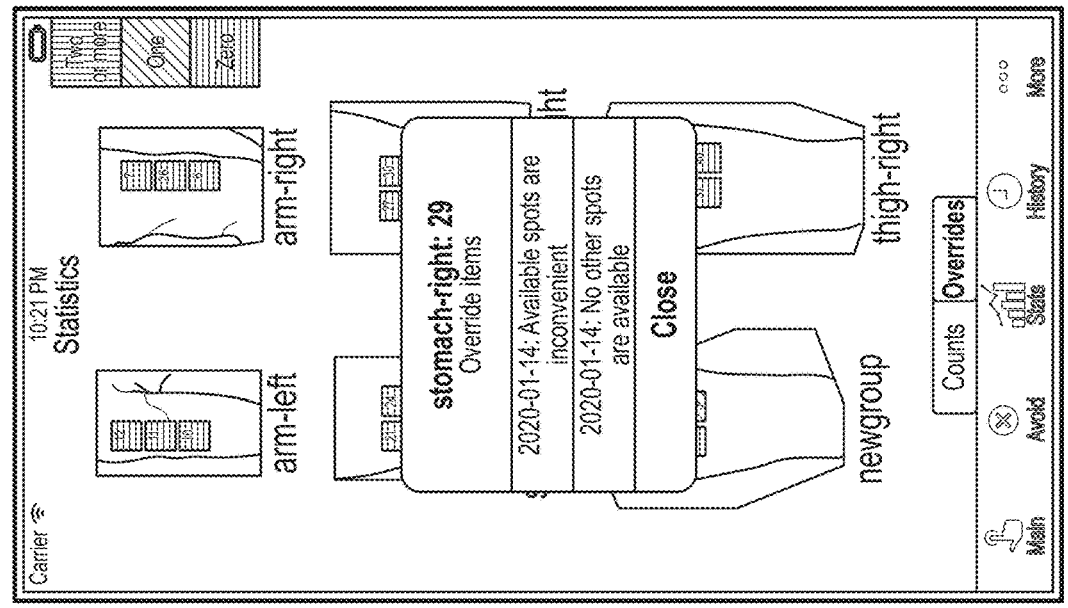
FIG. 12C illustrates an exemplary interface for reviewing override justifications associated with a site, in accordance with various embodiments.

Referring to FIG. 12B, statistics interface 1210 for tracking overrides of unavailable sites is shown, in accordance with various embodiments. Statistics interface 1210 may highlight sites 202 that were selected despite unavailability. For example, sites overridden two or more times may be red, sites overridden one time may be purple, and sites overridden zero times may be blue. Other count thresholds or predetermined tracking durations may be set to adapt statistics interface 1210 to habits of an individual user. Justifications for overriding unavailability may be accessed in response to an input selecting a spot with a nonzero override count, as shown in FIG. 12C. The user, a caretaker, a parent, or other person using insulin rotation application 110 may reference statistics interface 1210 to quickly assess an individual's habits in overriding unavailable site warnings.

Figure 13B:
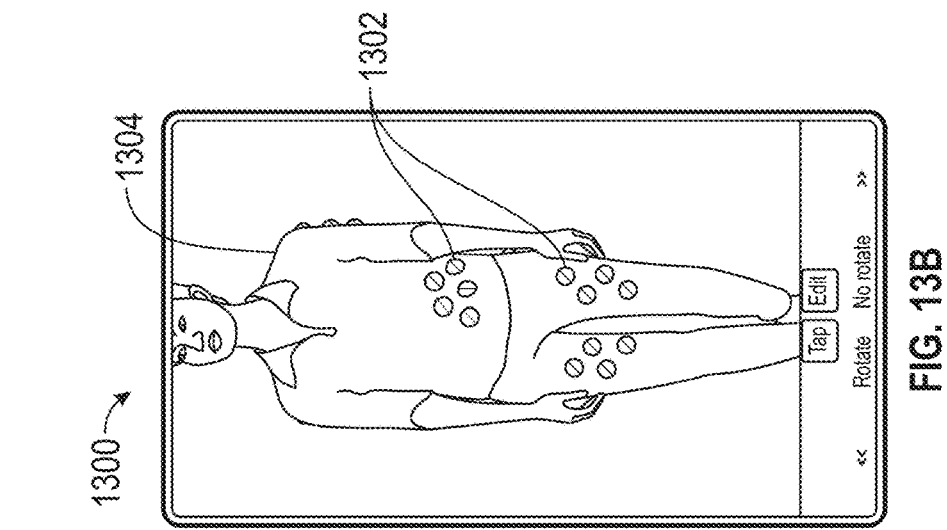
FIG. 13B illustrates an interface having a zoomed in 3-dimensional depiction of a body having insulin administration sites, in accordance with various embodiments.
Figure 13A:
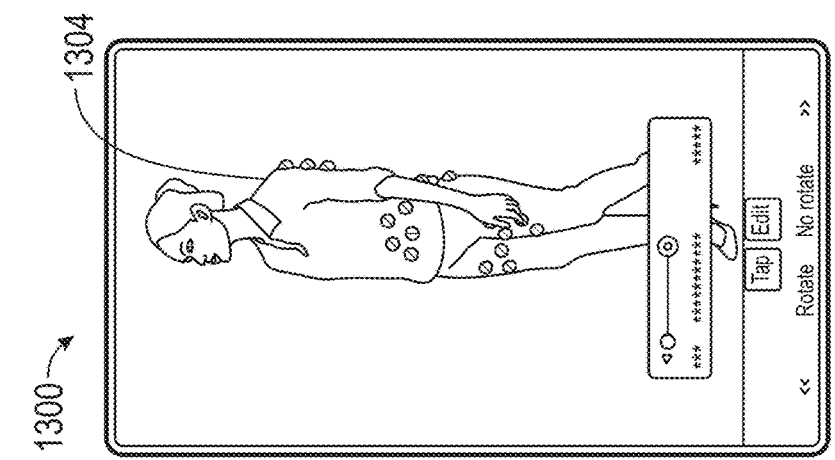
FIG. 13A illustrates an interface having a 3-dimensional depiction of a body having insulin administration sites, in accordance with various embodiments.
Figure 13C:
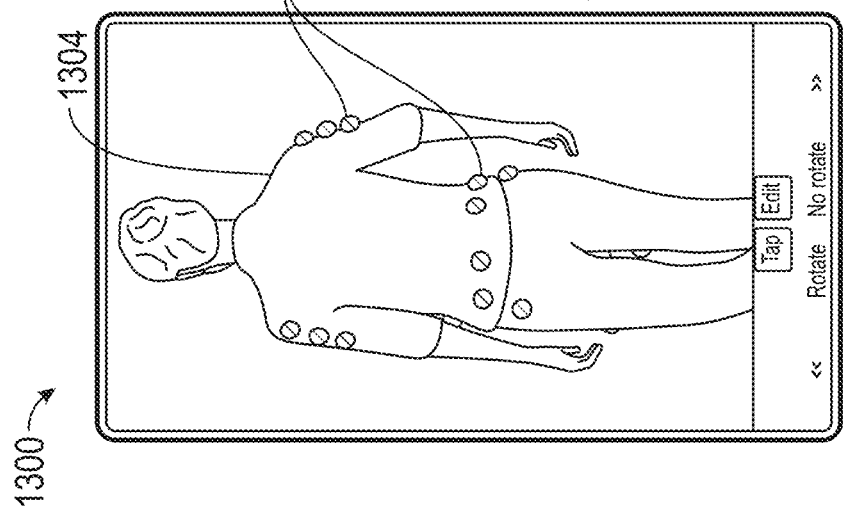
FIG. 13C illustrates an interface having a rotated 3-dimensional depiction of a body having insulin administration sites, in accordance with various embodiments.

Now with reference to FIGS. 13A-13C, an interface 1300 is shown for rendering insulin administration sites on a 3-dimensional model 1304 of body 106 (of FIG. 1A), in accordance with various embodiments. Application 110 (of FIG. 1A) may store locations of the sites 1302 (similar to sites 202 of FIG. 2) relative to the body 106 and historic usage of the sites 1302, as described herein with reference to 2-dimensional representations of the site 1302 information. A 3-dimensional representation may use the same or similar location information to display sites 1302 on a 3-dimensional model as on a 2-dimensional model.

In various embodiments, application 110 may manipulate the sites 1302 in response to user input and display 3-dimensional model 1304 from an altered point of view or perspective in interface 1300. For example, a user may rotate (as illustrated in transitioning from FIG. 13A to FIG. 13C) or zoom (as illustrated in transitioning from FIG. 13A to FIG. 13B) the 3-dimensional model 1304 using hand gestures, mouse movements, keystrokes, or other user input techniques. Sites 1302 may maintain exact or approximate location on body 106 in response to manipulation of 3-dimensional model 1304. When in edit mode, sites 1302 may be placed or deleted at will using interface 1300. For example, a user may tap on the desired location to add a new site 1302.

In various embodiments, functionality described above with reference to a 2-dimensional model or image may be used in conjunction with 3-dimensional model 1304 and/or interface 1300. For example, sites 1302 may be color coded to show usage status in a manner similar to or identical to sites 1302 shown using a 2-dimensional representation. A site 1302 may be selected for use just by tapping on the spot, and the spot may change color or give another visual cue in response to the selection.

Figure 14B:
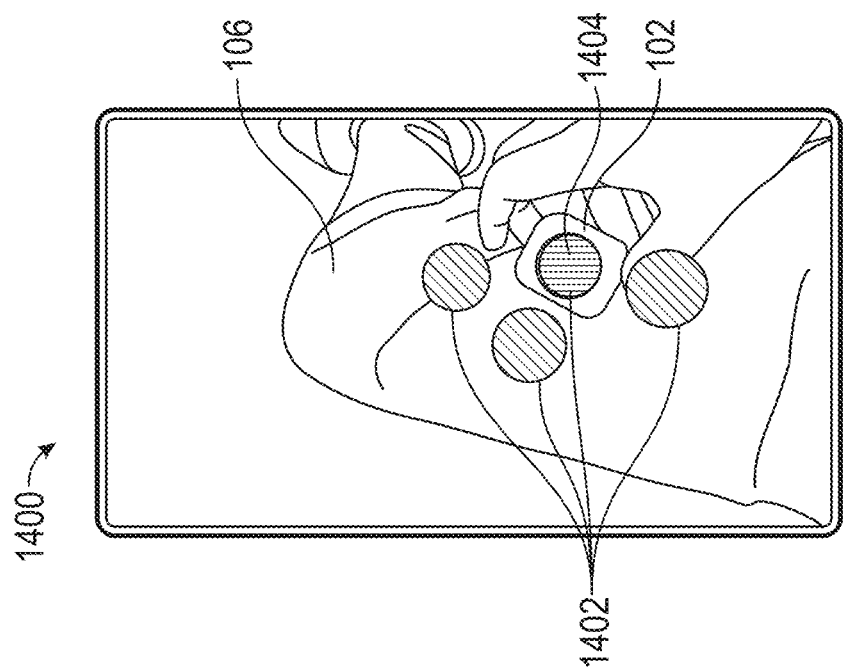
FIG. 14B illustrates an interface for selecting an insulin administration site using augmented reality, in accordance with various embodiments.
Figure 14A:
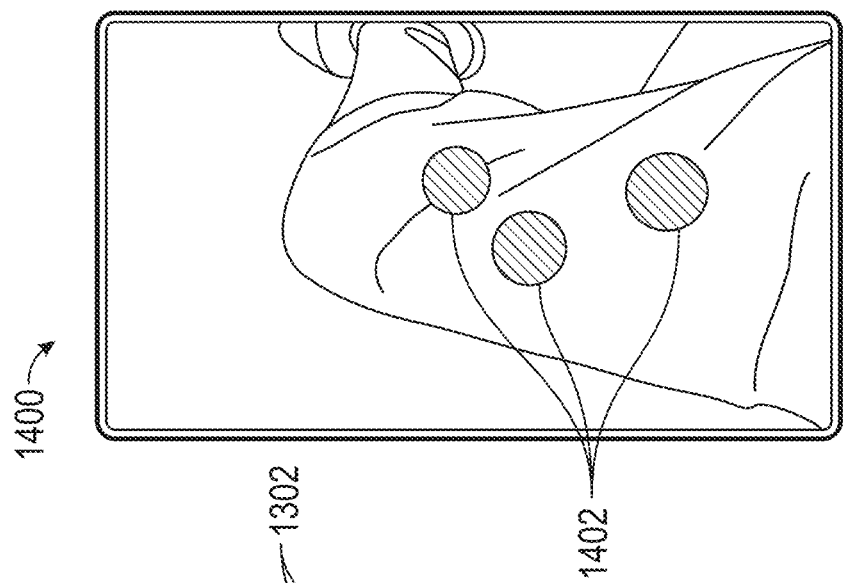
FIG. 14A illustrates an interface for assessing insulin administration site using augmented reality, in accordance with various embodiments.

With reference to FIGS. 14A-14B, interface 1400 is shown for placing insulin administration devices and tracking use of sites 1402, in accordance with various embodiments. Sites 1402 may be similar to sites 1302 of FIG. 13A and sites 202 of FIG. 2. Site selection using a static 3-dimensional or 2-dimensional model may allow for variance between the location at site 1402 in application 110 and the actual location on body 106 where insulin management device 102 is placed in response to a user estimating the location of insulin management device 102. An augmented reality feature of application 110 may improve the precision of site 1402 in application 110 reflecting the actual location on body 106 where insulin management device 102 is placed.

In various embodiments, a user may select a site 1404 in group 302 in the application 110. The site 1404 may change color or manifest other visual cues in application 110 to indicate the selection. The user may select the augmented reality feature of application 110. The augmented reality feature of application 110 may activate a camera of device 108. The camera may be an integral component of device 108 such as, for example, the camera on a smartphone or tablet. The camera may be a peripheral device coupled with device 108 through a wired or wireless connection.

In various embodiments, the camera may focus on the part of body 106 where the selected sites 1402 are located. Sites 1402 on parts of body 106 captured by the camera may move with the point of view of the camera and with the parts of body 106 such that sites 1402 are depicted in the same or nearly the same location relative to body 106 regardless of point of view or positioning of body 106.

In various embodiments, the real-time video image of body 106 captured by the camera may thus show the sites 1402 in the same or similar region as with the 3-dimensional model 1304 (of FIG. 13A) superimposed over parts of body 106 captured in the field of view of the camera. Device 108 and application 110 may present the real-time video image using interface 1400 (compared to the static images of interface 1300 in FIG. 13A). Locations on a body may be mapped using coordinates or other techniques suitable for retaining location information relative to a body. Locations may be rendered over different bodies and/or different clothing and still render accurately over parts of body 106 captured by the camera. Camera may capture parts of body 106 in direct field of view or through reflections in mirrors or other reflective surfaces.

In various embodiments, users may place insulin management device 102 on the selected group and/or site 1404 rendered over parts of body 106 in the real-time video image captured by the camera of device 108. For example, interface 1400 of FIG. 14A depicts frame of video with a left leg of body 106 having sites 1402 superimposed over the leg. Sites 1402 rendered over the leg may have different colors or other visual indicators to indicate different statuses such as, for example, selected, available, in use, unavailable, or other suitable site statuses. In some embodiments, a selected site 1404 may be rendered in a different shade or color than an unselected site having the same or similar status to visually indicate site 1404 is selected. The user may position insulin management device 102 on the selected site 1404. Site 1402 may be selected for placement in application 110 in response to a user touching or otherwise identifying site 1404 in interface 1400 of application 110.

In various embodiments, site 1404 may be identified by application 110 as being in use in response to a user placing insulin management device 102 on body 106 and application 110 recognizing that insulin management device 102 is placed at site 1404. Application 110 may detect site 1404 in use where insulin management device 102 is placed automatically using video processing techniques in response to insulin management device 102 being located over site 1404 on body 106 for a predetermined amount of time. Application 110 may detect site 1404 where insulin management device 102 is placed in response to a user capturing a still image or real-time video in interface 1400 with the insulin management device 102 in place over a site 1402.

In accordance with various embodiments and with renewed reference to FIGS. 1A and 1B, application 110 may assist patients in assessing blood glucose levels. Application 110 may track, detect, or interact with other applications to assess factors relevant to blood glucose levels such as, for example, carbohydrate intake, body weight, body mass index, exercise levels and frequency, form of the carbohydrates (i.e., the glycemic index), insulin sensitivity, age, genetic factors, past absorption rates, and time of day. Application 110 may use assessed factors to estimate insulin absorption rates at sites 1402 in various states of use or recovery.

Application 110 may monitor or track the appropriate amount of insulin required in various situations over time. Application 110 may integrate with an insulin pump that keeps track of carbohydrates consumed and insulin injected. Application 110 may can calculate the average insulin used for each gram of carbohydrate eaten while the pump was in use (i.e., insulin resistance). At locations on body 106 with tissue damage, the calculated insulin resistance may be higher due to the tissue damage resulting in reduced glucose control.

In various embodiments, application 110 may track of the location of the pumps over time and calculate the average insulin resistance at each site 1402 based on historic data at that site. Over time, application 110 may use the tracked data and results to form training set for machine learning. The machine learning system may estimate the insulin resistance at various locations where pumps are used, starting with a default estimate approach and refining in response to tracked results incorporated into the training sets.

In various embodiments, application 110 may create a site resistance map that predicts the insulin resistance levels at various sites 1402 on body 106. Application 110 may present the resistance map to a user. Application 110 may also suggest low-insulin-resistance sites 1402 for placement of an insulin pump or other insulin management device 102. Application 110 may suggest adjustments to insulin dosing based on the insulin resistance of a site 1402 in use by an insulin management device 102. By collecting data on factors relevant to blood glucose levels over time, application 110 may identify the differences in insulin resistance at different sites 1402. Application 110 may further identify different insulin resistance levels on different body areas such as, for example, the abdomen, thighs, upper arms, torso, or other suitable body areas.

In various embodiments, application 110 may use a statistical approach to monitor the insulin absorption kinetics at each site 1402. By combining site information with insulin pump data and glucose level data (e.g., from a continuous glucose monitor), application 110 may estimate site-specific insulin-on-board values to feed into closed-loop glucose control algorithms.

Application 110 takes a unique approach to the site rotation problem faced by many diabetics. Application 110 tends to reduce the likelihood of errors in tracking and rotating insulin administration and monitoring sites. Application 110 serves as an intuitive mechanism to select spots for pump, syringe, and glucose monitor placement, and application 110 keeps track of the site history for site rotation. Application 110 facilitates ease of setup through default configuration files and interfaces described herein. Site 1402 selection for placement of pumps, syringes, and continuous glucose monitors is tracked day-to-day for site rotation. Application 110 also integrates the history log 702 with insulin usage and continuous glucose monitoring data to provide insights into health and/or efficacy of sites 1402 at absorbing insulin. Application 110 tends to improve managing site rotation and guidance by pinpointing the best sites 1402 and/or available sites 1402 for absorption and glucose control.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions.

The scope of the invention is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Devices, systems, and methods are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or device that comprises a list of elements does not include only those elements but may include other elements not expressly listed or inherent to such process, method, article, or device.

What is claimed is:

1. A process for managing site rotation comprising:
    reading, by an application running on a device, a configuration file including a group, a plurality of sites in the group, and an image associated with the group;
    detecting, by the application running on the device, an input selecting a site from the plurality of sites for administration of an insulin management device;
    setting, by the application running on the device, an unavailable flag for the selected site for a predetermined duration in response to the input selecting the site; and
    writing, by the application running on the device, a log entry to track usage of the site in response to the input selecting the site.

2. The process of claim 1, further comprising:
    creating, by the application running on the device, a new image associated with the group; and
    overlaying, by the application running on the device, the sites in the group on the new image associated with the group.

3. The process of claim 1, further comprising displaying, by the application running on the device, a first visual indicator on the selected site to show that the site is recently selected in response to detecting the input selecting the site within a predetermined duration.

4. The process of claim 3, further comprising displaying, by the application running on the device, a second visual indicator on the selected site to show that the site is unavailable in response to a first period greater than the predetermined duration lapsing since detecting the input selecting the site.

5. The process of claim 4, further comprising setting, by the application running on the device, a recent parameter associated with the insulin management device in response to reading the configuration file; and
    displaying, by the application running on the device, a third visual indicator on the selected site to show that the site is available in response to a period greater than the recent parameter lapsing since detecting the input selecting the site.

6. The process of claim 1, further comprising:
    determining, by the application running on the device, an insulin diffusion sensitivity for the selected site; and
    estimating, by the application running on the device, an insulin-on-board value of the site to control an Artificial Pancreas Device System.

7. The process of claim 1, wherein the insulin management device comprises a pump, a syringe, a glucose monitor, a portable infusion pump, a cannula inserter, a needleless jet injector, a system with a separate drug reservoir, or an implantable drug pump.

8. The process of claim 1, further comprising sending, by the application running on the device, a notification to a second device in response to the insulin management device being in place longer than the predetermined duration.

9. The process of claim 1, further comprising overriding, by the application running on the device, the unavailable flag in response to receiving a justification from an override interface.

10. The process of claim 1, further comprising displaying a statistics interface comprising site counts, override justifications, and insulin usage by site.

11. The process of claim 1, further comprising estimating insulin diffusion sensitivity in response to insulin usage at the selected site, data from the insulin management device, exercise data, and carbohydrate data.

12. The process of claim 1, further comprising suggesting, by the application running on the device, the site for use in response to historic site usage and insulin diffusion sensitivity.

13. The process of claim 12, wherein the insulin management device generates closed-loop data to suggest the site for use.

14. A process for rotating insulin administration sites comprising:
    reading, by an application running on a device, a configuration file including a plurality of insulin administration sites having locations on a 3-dimensional model of a body;
    rendering, by the application running on the device, the plurality of sites over an image of a body part associated with the 3-dimensional model of the body;
    detecting, by the application running on the device, a selected site from the plurality of sites for placement of an insulin management device; and
    setting, by the application running on the device, an unavailable flag for the selected site for a predetermined duration in response to detecting the selected site.

15. The process of claim 14, further comprising rotating, by the application running on the device, the image of the body part associated with the 3-dimensional model in response to a user input.

16. A computer-based system for rotating insulin administration sites comprising:
    a processor; and
    a tangible, non-transitory memory configured to communicate with the processor, the tangible, non-transitory memory having instructions stored thereon that, in response to execution by the processor, cause the computer-based system to perform operations comprising:
    reading, by an application running on a device, a configuration file including a plurality of sites having locations on a 3-dimensional model;
    rendering, by the application running on the device, the plurality of sites over an image of a body associated with the 3-dimensional model;
    detecting, by the application running on the device, a selected site from the plurality of sites for administration of an insulin management device;

setting, by the application running on the device, an unavailable flag for the selected site for a predetermined duration in response to detecting the selected site; and writing, by the application running on the device, a log entry to track usage of the selected site in response to the detecting the selected site.

17. The computer-based system of claim 16, wherein the insulin management device comprises a portable infusion pump, a cannula inserter, a needleless jet injector, a system with a separate drug reservoir, or an implantable drug pump.

18. The computer-based system of claim 16, wherein the operations further comprise identifying, by the application running on the device, the selected site in response to historic site usage and insulin diffusion sensitivity at the selected site.

19. The computer-based system of claim 16, wherein the operations further comprise:

capturing, by a camera of the device, a video of a part of the body associated with the 3-dimensional model; and rendering, by the device, the plurality of sites over the video of the part of the body in real-time.

20. The computer-based system of claim 16, wherein the operations further comprise guiding a user with real-time video to place the insulin management device on the selected site.

\* \* \* \* \*